United States Patent

Matsui et al.

[11] Patent Number: 5,562,446
[45] Date of Patent: Oct. 8, 1996

[54] SMALL HANDPIECE WITH FLUID DRIVEN TURBINE

[75] Inventors: Akira Matsui, Kyoto; Yoshinori Morita, Shiga, both of Japan

[73] Assignee: J. Morita Mfg. Corp., Kyoto, Japan

[21] Appl. No.: 381,508

[22] Filed: Jan. 31, 1995

[30] Foreign Application Priority Data

Feb. 10, 1994 [JP] Japan .................................. 6-036404

[51] Int. Cl.$^6$ ...................................................... A61C 1/05
[52] U.S. Cl. ............................................ 433/132; 415/904
[58] Field of Search ...................................... 433/132, 106; 415/904, 25, 35

[56] References Cited

U.S. PATENT DOCUMENTS 3,128,988  4/1964  Mandroian ............................. 433/132
3,955,284  5/1976  Balson .................................... 433/132
4,786,251  11/1988  Ruegsegger ............................ 433/132

*Primary Examiner*—Cary E. O'Connor
*Attorney, Agent, or Firm*—Koda and Androlia

[57] ABSTRACT

A small handpiece with a fluid driven turbine is composed of a head portion and a neck portion connected continuously to the head portion. The head portion has a head defining a chamber therein, turbine blades mounted on a turbine rotor shaft and arranged within the chamber and the turbine rotor shaft rotatably supported in the head via bearing portions. The neck portion has a main body, a supply channel arranged in the main body to supply compressed fluid to the turbine blades within the chamber and an exhaust channel arranged in the main body to discharge the compressed fluid from the chamber. The supply channel has a single supply port. A positional relationship between the single supply port and an exhaust port of the exhaust channel is set so that the exhaust port is arranged at a position proximal to the supply port.

18 Claims, 15 Drawing Sheets

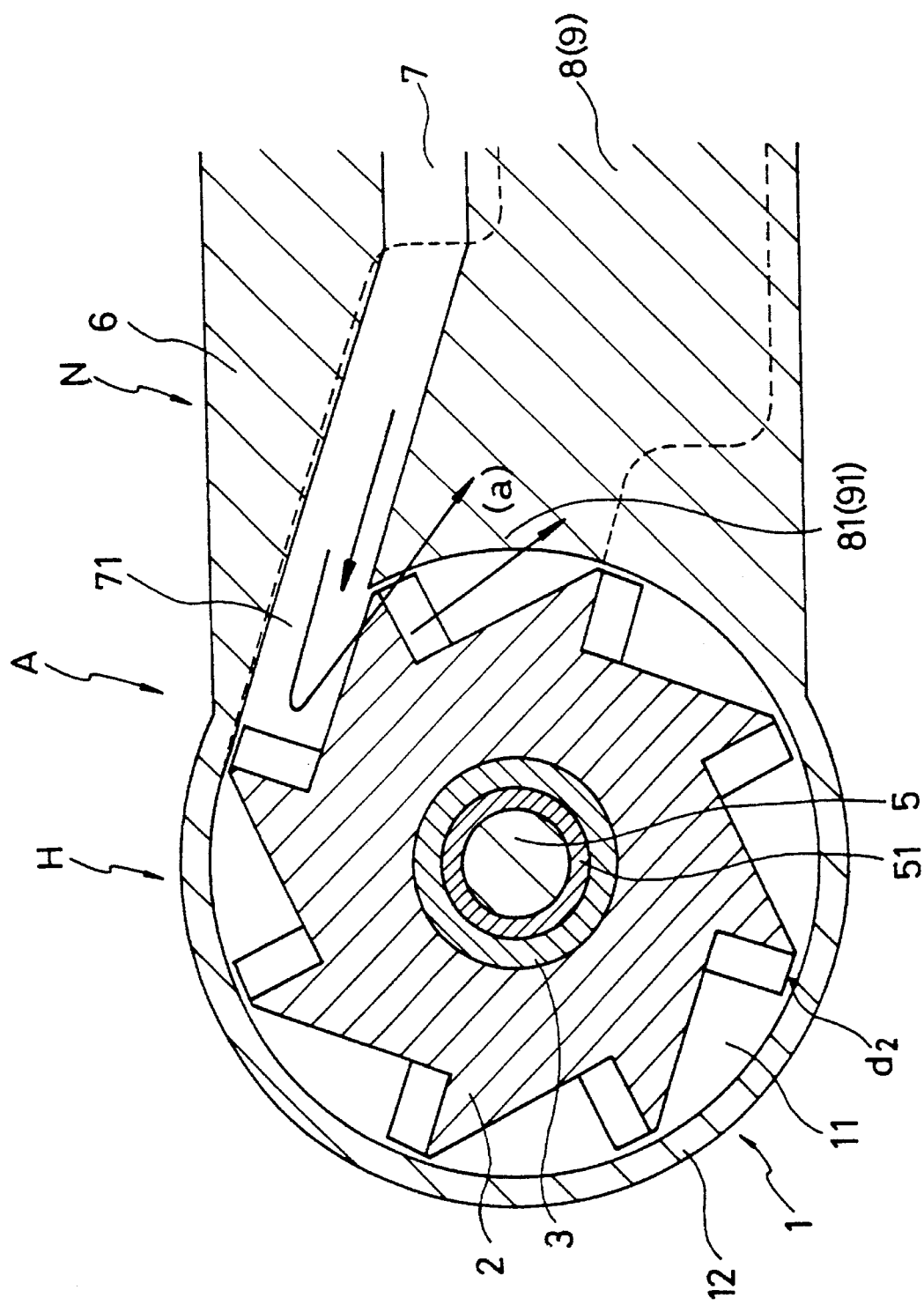

SUPPLY AIR VELOCITY VERSUS SUPPLY AIR PRESSURE
Exhaust port diameter: 2.5mm, normal pressure, 25 °C
(theoretical values)

(NOTE)
Supply port diameter (cross-sectional area):
(1) ——————— 0.9 mm (0.64 mm$^2$)
(2) ------------- 1.2 mm (1.13 mm$^2$)
(3) —·—·—·— 1.5 mm (1.77 mm$^2$)

SMALL HANDPIECE WITH FLUID DRIVEN TURBINE

BACKGROUND OF THE INVENTION (i) Field of the Invention

This invention relates to a small handpiece of the fluid driven turbine type useful for handcrafting or medical or dental treatment (hereinafter called "the small handpiece with a fluid driven turbine").

More specifically, this invention is concerned with a small handpiece with a fluid driven turbine, which has been dimensionally reduced by itself, has made it possible to increase within a head chamber the speed of turbine blades, that is, the output torque of a turbine rotor shaft having the turbine blades on a peripheral wall portion thereof and one of various tools in an axially-extending central portion thereof under supply of smaller energy, and shows high performance despite its small dimensions.

(ii) Description of the Related Art

Small handpieces with a fluid driven turbine have been used widely to date, for example, for cutting and/or grinding materials or, as medical or dental applications, for open-cutting, trepanating, cutting or severing bones or teeth upon conducting restorative operations in surgery (cerebral surgery, plastic surgery, laryngeal surgery or otolaryngology) or upon performing intraoral treatments in dentistry.

Among the above-mentioned small handpieces with a fluid driven turbine, small dental handpieces with a fluid driven turbine in which compressed air is used as the compressed fluid, i.e., a drive medium for the turbine, for example, are called "dental air turbine handpieces". They have an external appearance as shown in FIG. 1, which will be referred to upon describing the technical constitution of the present invention subsequently herein.

As is illustrated in FIG. 1, the dental air turbine handpiece A, described specifically, is composed of a head portion H and a grip portion G. A neck portion N of the grip portion G is connected continuously to the head portion H and is internally equipped with means for supply compressed air to air turbine arranged within the head H and discharging the compressed air from the head H. Designated at B in FIG. 1 is a tool fixedly held on a rotor shaft of the air turbine.

A description will hereinafter be made of the conventional art and the present invention by taking, for the convenience of description, the above-mentioned dental air turbine handpiece, which makes use of compressed air as a drive medium for the turbine, as a representative example of small handpieces with a fluid driven turbine.

Needless to say, the drive medium for the turbine is not limited to the above-mentioned compressed air in the present invention.

Namely, the compressed fluid as a drive medium for a turbine is not limited to compressed air but various compressed fluids, for example, compressed liquids and compressed gases including compressed steam, can be used.

The terms "air supply" and "air supply port" and the terms "air exhaust (discharge)" and "air exhaust port" as used in relation to compressed air in the subsequent description must therefore be read obviously as "supply" and "supply" port and "exhaust (discharge)" and "exhaust port" where other compressed fluids are applied.

Applications of small handpieces with a fluid driven turbine, which pertain to the present invention, are not limited to the above-mentioned dental field but are found in the medical field and also fields where materials are cut and/or ground.

In these application fields, the small handpieces according to the present invention can be used, needless to say, not only in a hand-held manner in association with the term "handpieces" but also as elements (members, parts or the like) of equipments.

A conventional dental air turbine handpiece A', especially, the internal construction of its head portion H' and its neck portion N' connected continuously to the head portion H' is illustrated in FIGS. 16 and 17.

In FIGS. 16 and 17 which illustrate the internal construction of the conventional dental air turbine handpiece A', FIG. 16 is a vertical cross-sectional view as viewed in the direction of an axis of a turbine rotor shaft 3' whereas FIG. 17 is a cross-sectional view taken in the direction of arrows XVII—XVII of FIG. 16.

As is depicted in FIG. 16, the head portion H' of the conventional dental air turbine handpiece A' has turbine blades 2' mounted on a peripheral wall of the turbine rotor shaft 3' and arranged in a chamber 11' of a head 1' and rotatably supports the turbine rotor 3' via bearings 4' disposed inside the head 1'.

The head 1' is composed of a head main body 12' and a cap portion 13'. Inside the head main body 12', the chamber 11' is formed to accommodate the turbine blades 2' and the bearings 4' are also arranged to rotatably support the turbine rotor shaft 3'.

Needless to say, a tool shaft 5' of a dental cutting or grinding tool or the like is fixedly held in an axially-extending central portion of the turbine rotor shaft 3' to perform various treatments. In addition, a chuck 51' for holding the tool shaft 5' as shown in the drawings is arranged on a peripheral wall of the tool shaft 5'. Although the illustrated chuck is a frictional check mechanism, a known touch-actuated chuck mechanism can also be used.

As is shown in FIG. 16, each bearing 4' is formed of a ball bearing which is in turn constructed of an inner race 41', an outer race 42', balls 43' and a retainer 44'. Along an outer peripheral wall or an end portion of each bearing 4', an O-ring or a known mechanism for enhancing the axial stiffness may be arranged to make the bearing 4' centripetal. Although the illustrated bearings are ball bearings making use of balls 43', they can be any known air bearing mechanism called an "air bearing".

A matter which requires special consideration in the structure of the conventional dental air turbine handpiece A' shown in FIG. 16 is the manner of arrangement of the supply and exhaust system for the compressed air and also the manner of arrangement of the turbine blades 2' in association with the supply and exhaust system within the chamber 11'.

The conventional art is characterized in that as shown in FIG. 16, the turbine blades 2' are arranged with an extremely large interval ($d_1'$) left between the turbine blades 2' and each of upper and lower, inner walls 111', 112' as viewed in the direction of the axis of the turbine rotor shaft 3'. In the drawing, the interval ($d_2'$) between a peripheral inner side wall 113' of the chamber 11' and the turbine blades 2' is generally narrower than the above-mentioned interval ($d_1'$).

In conventional products, for example, those having a turbine blade (2') height of 2.8 mm as viewed in the direction of the axis of the turbine rotor shaft 3', there are known products in which the interval ($d_1'$) is 1.150 mm (1150 μm).

The above-described interval ($d_1'$) in the conventional products is extremely large compared with the corresponding interval in products according to the present invention. Its reason will be described subsequently herein when an air supply and exhaust system, the greatest characteristic feature of the present invention, is described.

As is illustrated in FIGS. 16 and 17, the neck portion N', specifically, its neck main body 6' is composed of one having:

an air supply channel 7' and an air supply port 71', both for supplying compressed air to the turbine blades 2' arranged within the chamber 11', and an air exhaust channel 8' and an air exhaust port 81', both for exhausting compressed air from the chamber 11'.

It is to be noted that precisely speaking, the expression "for exhausting compressed air from the chamber 11'" is not correct, because the compressed air supplied from the air supply port 71' into the chamber 11' undergoes abrupt expansion and depressurization upon passing through the air supply port 71' and does not maintain the compressed state which the compressed air had at the time of its supply.

In the subsequent description, however, the above expression will be adopted in relation to the expression "compressed air supplied through the air supply port". Likewise, a flow of air in the chamber will also be described using the term "compressed air stream".

In the conventional dental air turbine handpiece A' described above, the head main body 12' of the head portion H' or the main body 6' of the neck portion N' may be provided with a lighting system for lighting a site under treatment or with a water supply channel for spraying water or physiological saline to a site under treatment so that cutting or grinding heat of a bone or tooth can be eliminated or the bone or tooth can be washed.

FIG. 17 illustrates the manner of supply and exhaust of compressed air in the conventional dental air turbine handpiece A'.

Described specifically, the supply and exhaust of compressed air in the conventional dental air turbine handpiece A' are conducted in the manner illustrated in the drawing, that is, by supplying the compressed air to the supply channel arranged in the main body 6' of the neck portion N', guiding the compressed air through the supply port 71' into the chamber 11', injecting the compressed air against the blades 2' to produce rotational drive force on the turbine rotor shaft 3' and then exhausting the compressed air from the chamber 11'.

Namely, the supply of compressed air against the turbine blades 2' and the exhaust of the compressed air from the chamber 11' in the conventional air turbine handpiece A' are conducted assuming as a prerequisite the existence of the air supply and exhaust system shown in FIG. 17.

The air supply and exhaust system will now be described in detail. As is depicted in FIG. 17, compressed air is injected against the turbine blades 2', which are arranged within the chamber 11', from the air supply channel 7' arranged in the main body 6' of the neck portion N' and then through the air supply port 71', the compressed air is caused to take a U-turn while flowing about the turbine rotor shaft 3' inside the chamber 11', and is then guided from the exhaust port 81', which is arranged in the main body 6' of the neck portion N', to the exhaust channel 8' for exhaustion. In FIG. 17, streams b of the compressed air within the chamber 11' are shown, in which solid lines indicate a circumferential flow through the interval $d_2'$ (see FIG. 16) and a dashed line designates a circumferential flow through the interval ($d_1$) (see FIG. 16).

In the compressed air supply and exhaust system of the conventional dental air turbine handpiece A', compressed air is, as shown in FIG. 17, caused to take a U-turn (circumferential flows indicated by solid lines and the dashed line) while circumferentially flowing about the turbine rotor shaft 3' from the supply port 71' to the exhaust port 81' within the chamber 11' as indicated by the arrows b. This is believed to be attributable to the existence of the way of thinking as a fundamental that the flows of the compressed air continue to supply drive energy to the turbine blades in the course of their circumferential flows and hence to contribute to an increase in the rotational torque of the turbine rotor shaft 3'.

Since the compressed air supply and exhaust system of the conventional dental air turbine handpiece A' is based on the above-described way of thinking (design concept), the exhaust port 81' is arranged so that the compressed air injected through the supply port 71' is exhausted after the compressed air has flowed circumferentially in the chamber 11', specifically at the position shown in FIGS. 16 and 17.

Namely, as is shown in FIGS. 16 and 17, the exhaust port 81' is arranged at a position substantially symmetrical with the supply port 71' with a predetermined interval (C) left therebetween.

In view of the efficiency of transmission of moving energy from the compressed air to the turbine blades 2' and also the efficiency of exhaustion of the compressed air from the chamber, the supply port 71' is arranged so that as shown in FIG. 16, the compressed air is injected against substantially central parts of the turbine blades 12' as viewed in the direction of the axis of the turbine rotor shaft 3', whereas the exhaust port 81' is arranged at a position which is common in the central level to the supply port 71' and is spaced from the supply port 71' by the above-described interval (C). In view of the efficiency of exhaustion, an exhaust port generally has a greater opening area than an associated supply port.

To achieve an increase in the rotational torque (output) of the turbine rotor shaft 3' in the dental air turbine handpiece A' equipped with the air supply and exhaust system based on the conventional design concept described above, it is only necessary, theoretically speaking, to increase the supply velocity of the compressed air at the air supply port 71' or to increase the supply amount of the compressed air per unit time.

The rationale is that the force which the turbine rotor shaft 3' receives from the compressed air so supplied is equal to the moving energy which the turbine blades 2' receive from the streams of the compressed air per unit time, in other words, to the product of the supply velocity of the compressed air and the supply (inducted) volume of the air per unit time.

Further, the above-mentioned supply air velocity and supply (inducted) air volume are, as shown in FIGS. 18 and 19, dependent on the pressure of the compressed air so supplied and the cross-sectional area of the supply port. To achieve an increase in the torque (output), it is therefore only necessary to increase the pressure of the compressed air or to enlarge the cross-sectional area of the supply port. These measures have been adopted as routine approaches.

FIGS. 18 and 19 have been prepared as will be described next. In a system in which compressed air is supplied from a compressor and is injected into a chamber, an isentropic flow of compressible inviscid gas (i.e., a reversible flow not accompanied by any friction in an adiabatic system) was hypothetically considered. By using:

an equation obtained by introducing "conditions for an isentropic flow" and "the equation of state of a gas" into an energy equation which had been obtained by integrating the Euler's equation of motion on a one-dimensional steady flow of compressible inviscid gas along a stream line, that is, into the Bernoulli's equation, and the Euler's equation of continuity for a one-dimensional steady flow, were determined flow velocities at an air supply port of the chamber (air supply velocities corresponding to predetermined compressed air pressures) (see FIG. 18) and mass flow rates (air supply volumes corresponding to predetermined compressed air pressures) (see FIG. 19). These flow velocities and mass flow rates were then plotted into graphs.

Phenomena which are to be described next are however actually observed when one attempts to increase the above-mentioned supply air velocity and supply air volume in a dental air turbine system accommodated in a chamber having air supply and discharge ports of predetermined sizes and a predetermined capacity.

Incidentally, the following observation results were obtained by conducting experiments while using an experimental apparatus fabricated with a transparent synthetic resin by copying, as an air turbine system, the conventional dental air turbine handpiece A' described above with reference to FIGS. 16 and 17, specifically, "JET MASTER FAR-E2" (trade name; manufactured by J. MORITA MFG. CORP.).

(1) When the pressure of compressed air was raised to increase the supply air velocity:

As is appreciated from FIG. 18, it was unable to increase the supply air velocity beyond the velocity of sound even if the pressure of compressed air was raised beyond 1 kgf/cm$^2$. Compressed air pressures higher than the above level therefore do not contribute to an increase in torque.

(2) When the pressure of compressed air was raised to increase the air supply volume:

The above-described proportionality began to break, leading to a deterioration in the efficiency of transmission of energy from the supplied air.

Described specifically, the compressed air so supplied was unable to increase the torque (maximum speed) of the turbine rotor 3' in proportion to an increase in the air supply volume, for example, in proportion to the increase in the air supply volume achieved by changing the pressure of compressed air from 2.0 kgf/cm$^2$ to 3.0 kgf/cm$^2$ shown in FIG. 19.

This can be attributed to the following reasons:

(i) An increase in the air supply volume leads to an increase in the pressure within the chamber 11' and, as a result, a decrease is caused to occur in the supply air velocity.

(ii) The compressed air so supplied collides against the turbine blades 2' and then circumferentially flows within the chamber 11' in the same direction as the direction of rotation of the turbine rotor shaft 3'. Compared with the speed of the turbine rotor shaft 3', the velocity of the circumferential flow is however extremely low so that the circumferential flow conversely begins to act as a resistance inside the chamber. This resistance becomes greater with the pressure of compressed air.

(3) When the cross-sectional area of the air supply port was made greater to increase the air supply volume:

The compressed air so supplied began to act as a resistance in the chamber 11' as in the situation (2) described above. This tendency was however stronger than the above situation (2) that the pressure of compressed air to be supplied was increased.

This can be attributed to the fact that when the cross-sectional area of the air supply port increases, the compressed air injected through the air supply port is allowed to rapidly spread in the chamber 11' and its velocity is hence reduced to strengthen the resisting action. Accordingly, compressed air injected through a large air supply port encounters the above-mentioned resisting action, whereby the efficiency of transmission of energy from the supplied air to the turbine blade 2' is deteriorated further than the above-described situation (2).

Conventional techniques featuring enlargement of the air supply port as described above under (3) include, for example, the dental air turbine handpiece having dual air supply channel systems proposed in U.S. Pat. Nos. 3,893,242 and 4,020,556 to Lieb et al.

Each of the above U.S. patents provides the construction of the dental air turbine handpiece with new characteristic features in a wrench mechanism for fixing a took shaft on a turbine rotor shaft, an optical fiber system assuring efficient transmission of light (especially, connector means for optical fiber bundles in the interior of a handle portion, namely, a grip portion) and means for supplying compressed air to a turbine. FIGS. 2, 3 and 9 of the U.S. patents disclose an embodiment with the dual air supply channel systems (hence, having two air supply ports), in other words, an embodiment in which the cross-sectional area of the air supply port has been enlarged to increase the supply (inducted) volume of compressed air.

More specifically, the dental air turbine handpiece in each of the above U.S. patents has the structure that two air supply channels are arranged in the same horizontal plane relative to a turbine housing, in other words, two air supply ports are arranged at a desired angle relative to each other, compressed air is injected from each of the air supply ports against turbine blades disposed in the turbine housing and located in adjacent to the air supply port to apply rotating force to the turbine, and the air is then exhausted through exhaust ports.

In view of the description of the specification of each of the U.S. patents and FIGS. 3 and 9 in the patent, the exhaust ports are arranged above and below the air supply port, respectively.

A description is now made of significant differences in construction between the dental air turbine handpiece disclosed in the above U.S. patents and that of the present invention. These differences lead substantial differences in advantageous effects therebetween. This matter will be described in detail subsequently herein on the basis of substantiating data.

Compared with the dental air turbine handpiece according to the present invention, that disclosed in the U.S. patents is different in the following points:

They are totally different in the supply and discharge system for compressed air. Described specifically, the present invention has a single air supply port, whereas the U.S. patents have two air supply ports and the respective air supply ports are arranged at such positions as injecting compressed air against adjacent blades.

Attention is now drawn to the interval ($d_1'$) between the turbine blades disposed within the chamber and each of the upper and lower, inner walls of the chamber, which has been described above with reference to FIG. 16. In view of FIGS. 3 and 9 of the U.S. patents, especially, the interval ($d_1'$), the handpiece disclosed in the U.S. patents is considered to employ an air supply and exhaust system which belongs to the conventional art.

They are absolutely different from each other in the size of the compressed air supply port. In this respect, the U.S. patents do not disclose any specific quantitative values with respect to the sizes of the two air supply ports. In view of the embodiments of FIGS. 3 and 9, however, the U.S. patents disclose air supply ports having a size (diameter of each air intake port) equivalent to about 50% of the height of the turbine blades as viewed in the direction of the axis of the turbine rotor shaft. The total size of the two supply ports is considerably large.

The handpiece according to the present invention, on the other hand, is provided with only one air supply port as described above. Further, the size of the single air supply port is as small as about 50% of the height of the turbine blades.

As is evident from the foregoing, the dental air turbine handpiece of the U.S. patents was constructed in a way of thinking totally different from the below-described design concept of the present invention, and is believed to have adopted the approach that the number of air supply ports is increased to enlarge the overall cross-sectional area of air supply ports, in other words, to have adopted the approach that the cross-sectional area of an air supply port is increased to make the air supply volume greater for an increase in the torque of the turbine rotor shaft.

The above U.S. patents, however, exerted ingenuity in the manner (positions) of arrangement of the two air supply ports. Compared with simply enlarging the cross-sectional area of a single air supply port as explained above under (3), the compressed air so supplied is allowed to spread at a lower rate in the chamber 11'. The efficiency of transmission of energy from the compressed air so supplied is hence improved correspondingly, but is still poor.

In the conventional dental air turbine system, it may also be contemplated for the elimination of the above-described drawback to make the air exhaust port greater relative to the air supply port so that the resisting action of the compressed air can be eliminated.

If the air exhaust port is made larger relative to the air supply port, however, the compressed air injected from the air supply port is allowed to rapidly spread in the chamber and is then exhausted. The amount of compressed air which collides against the turbine blades 2' is therefore decreased, so that the efficiency of transmission of the energy of the compressed air so supplied is deteriorated, resulting in a sharp decrease in the torque (output) of the turbine rotor 3'.

Limitations, which the conventional are described above with reference to FIGS. 16 and 17 and various improvements including those proposed in the above U.S. patents are accompanied with, will be described subsequently herein on the basis of substantiating data upon description of the technical features of the present invention.

SUMMARY OF THE INVENTION

An object of the present invention is to overcome the limitations of the conventional art (the conventional design concept), said limitations being observed on small handpieces with a fluid driven turbine for dental and other applications, and to provide, on the basis of a totally new design concept, a small high-performance handpiece with a fluid driven turbine.

The present invention has been completed based on the finding that in a small handpiece with a fluid driven turbine, for example, a dental air turbine hand-piece, reconstruction of the supply and exhaust system for compressed air, in particular, in a totally new way of thinking makes it possible to reduce the size of the turbine system compared with the conventional turbine system of the same type and further to achieve a considerable improvement in the efficiency of transmission of energy from supplied air to the turbine rotor shaft, hence, an increase in the torque (i.e., output).

Describing in short, the present invention therefore provides a small handpiece (A) with a fluid driven turbine, said handpiece being composed of a head portion (H) and a neck portion (N) connected continuously to said head portion (H), said head portion (H) having a head (1) defining a chamber (11) therein, turbine blades (2) mounted on a turbine rotor shaft (3) and arranged within said chamber (11) and said turbine rotor shaft (3) rotatably supported in said head (1) via bearing portions (4), and said neck portion (N) having a main body (6), a supply channel (7) arranged in said main body (6) to supply compressed fluid to said turbine blades (2) within said chamber (11) and an exhaust channel (8) arranged in said main body (6) to discharge the compressed fluid from said chamber (11), characterized in that:

(i) said supply channel (7) has a single supply port (71); and (ii) a positional relationship between said single supply port (71) and an exhaust port (81) of said exhaust channel (8) is set so that said exhaust port (81) is arranged at a position proximal to said supply port (71).

The present invention, namely, the small hand-piece with the fluid driven turbine for dental and other applications has been completed based on a design concept which is totally different from the conventional design concept.

In particular, the present invention has modified the compressed fluid supply and exhaust system for the turbine blades of the turbine rotor shaft, said turbine blades being arranged in the chamber of the head portion of the handpiece, so that immediately after collision of the compressed fluid against the turbine blades, the compressed fluid is promptly exhausted from the chamber to avoid negative influence to the rotation of the turbine blades within the chamber.

By the above-described supply and exhaust system, more specifically, by the new manner of arrangement of the supply port and the exhaust port, the small hand-piece with the fluid driven turbine, according to the present invention, can considerably improve the speed of the turbine rotor shaft (in other words, the torque) over the conventional ones under the same supply pressure and supply volume of compressed fluid.

Owing to the above-mentioned significant improvement in the speed of the turbine rotor shaft, the small handpiece with the fluid driven turbine, according to the present invention, has brought about numerous excellent advantages such as a reduction in rotating noise (i.e., a reduction in the noise produced from the handpiece), lessening in the requirement for high pressure resistance to an air supply tube, an improvement in handling ease owing to the usability of a flexible air supply tube (this advantage is associated with the advantage described immediately above), quick treatment under large torque, the provision of a portable hand-piece of the fluid cylinder driven type because the same torque as that available from the conventional handpieces can be obtained even by small fluid energy, and a dimensional reduction in equipments.

BRIEF DESCRIPTION OF THE DRAWINGS

FIG. 3 is a cross-sectional view taken in the direction of arrows III—III of FIG. 2;

DETAILED DESCRIPTION OF THE INVENTION

Figure 1:
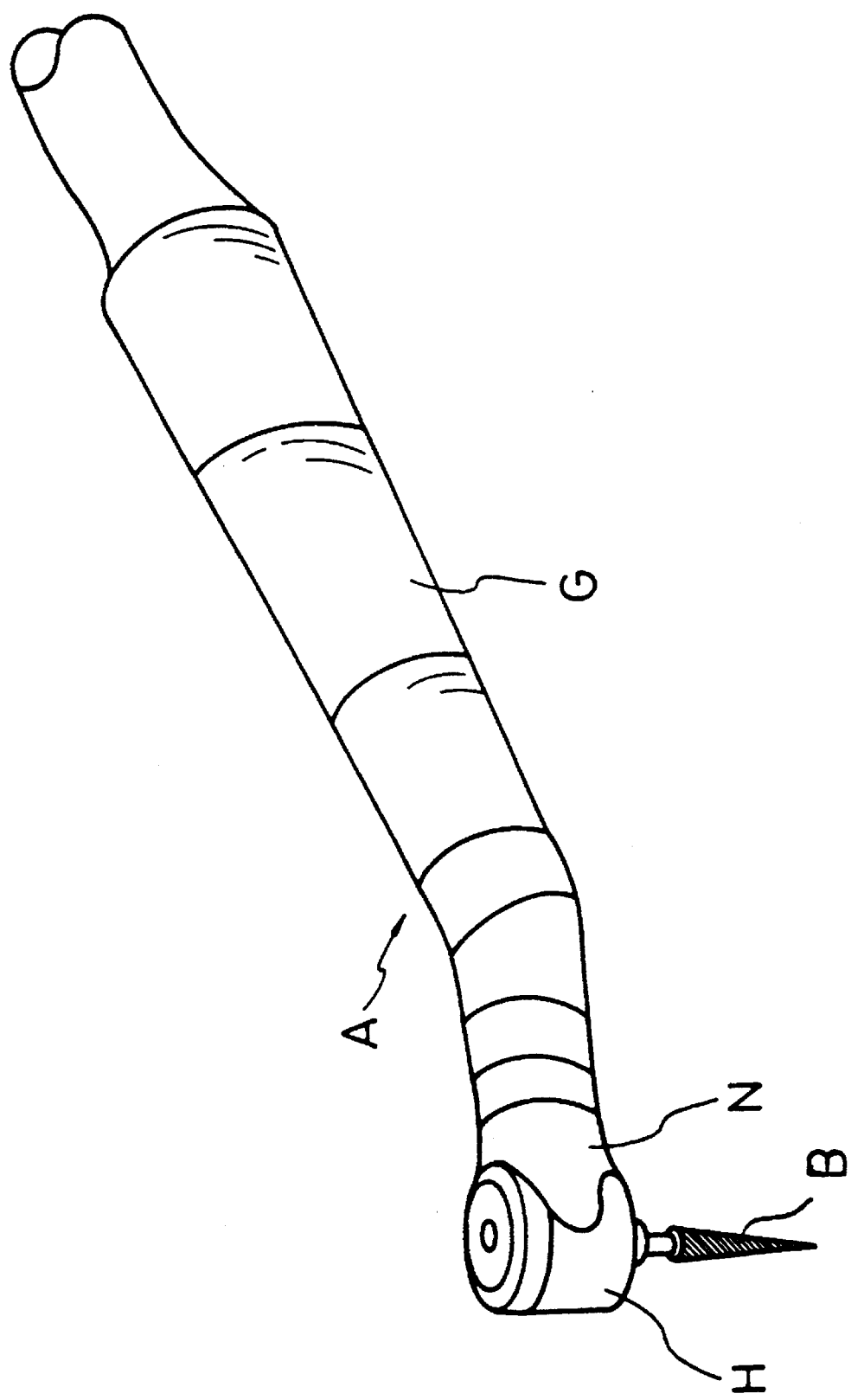
FIG. 1 is a perspective view of a small (dental) air turbine handpiece according to the present invention.

The technical features and embodiments of the present invention will hereinafter be described in detail with reference to the drawings while still making reference to the dental air turbine handpiece described above.

Needless to say, it should be borne however in mind that the present invention is not limited to the embodiments illustrated in the drawings.

The beginning of this invention by the present invention resides in the finding of the following matters as a result of experiments which was conducted by placing foamed polystyrene resin balls of a small diameter in compressed air or in the chamber of the experimental apparatus which had been fabricated with the transparent synthetic resin by copying the conventional dental air turbine handpiece described above with reference to FIGS. 16 and 17, specifically, "JET MASTER FAR-E2" (trade name; manufactured by J. MORITA MFG. CORP.).

(i) Where the pressure of supplied compressed air was up to 0.5 kgf/cm$^2$ (10–25 l/min), the compressed air was observed to circumferentially flow in a direction opposite to the direction of rotation of the turbine rotor about the turbine rotor shaft in the chamber subsequent to its collision against the turbine blades. This air flow acted as a resistance to rotation of the turbine rotor.

(ii) When the pressure of supplied compressed air exceeded 0.5 kgf/cm$^2$, both the rotating noise and the noise of the air supply and exhaustion abruptly changed and at the same time, the compressed air began to circumferential flow in the same direction as the direction of rotation of the turbine rotor in the chamber. The velocity of the resulting circumferential flow was however extremely low compared with the speed of the turbine rotor.

(iii) With a view toward making an improvement in the speed (torque) of the turbine rotor, the pressure of compressed air to be supplied or the inducted volume of compressed air was increased. When the pressure of compressed air to be supplied was increased, for example, to 2.5 kgf/cm$^2$ (45 l/min) or higher, the air pressure within the chamber arose so that the compressed air so supplied and inducted behaved as if it acted as a resistance in the chamber (in other words, the compressed air gave no substantial contribution or only a negative contribution to an increase in the torque).

(iv) When the exhaust port was enlarged to improve the above phenomenon (iii), the air pressure within the chamber became lower. Conversely, a reduction in the torque was however observed because the compressed air injected from the air supply port was allowed to promptly spread and was then exhausted.

With a view toward reducing or eliminating the above-described negative effects (iii) and (iv), the present inventors conducted a study by going back even to the design concept of the conventional dental air turbine handpiece.

The conventional design concept has been described above in detail under the Description of the Related Art.

As a result, the present inventors have found that in the supply system of compressed air to the turbine blades and the exhaust system of compressed air from the chamber, especially the exhaust system of compressed air from the chamber in the conventional dental air turbine handpiece, a far superior advantageous effect, specifically, a high efficiency of energy transmission from supplied air (an increase in torque) can be achieved when a modification is made:

from the conventional type that compressed air is caused to circumferentially flow in the chamber (hereinafter also called "the circumferential flow type" and the conventional manner of arrangement of the air supply port and the air exhaust ports determined in view of the circumferential flow type, to the type that compressed air is prevented as much as possible from circumferentially flowing in the chamber (this flow type of this invention will hereinafter be called "the non-circumferential flow type" to distinguish it from the conventional circumferential flow type) and the manner of arrangement of an air supply port and an air exhaust port determined in view of the non-circumferential flow type.

In the conventional circumferential flow type, a large space is left between the housing member of the chamber and the turbine blades (see the interval $d_1'$ in FIG. 16) to allow the compressed air to circumferential flow in the chamber. The non-circumferential flow type makes it possible to eliminate this space, resulting in the finding that the above-described excellent advantageous effect can be brought about with a turbine system of still smaller dimensions.

This invention is based on the above-described findings and study results of the present inventors, and is totally different from the conventional approach.

The dental or like, small handpiece with the fluid driven turbine, according to the present invention, has adopted the non-circumferential flow type and also the compressed fluid supply and exhaust system designed in view of the non-circumferential flow type.

More specifically, the manner of arrangement of the supply port and the exhaust port for compressed fluid under the non-circumferential type of this invention has been developed under a design concept totally different from the conventional design concept, that is, under the design concept that after injecting the compressed fluid from the supply port against the turbine blades rotatably arranged in the chamber and hence applying rotational force to the turbine rotor shaft, the compressed fluid is promptly discharged through the exhaust port instead of allowing it to circumferentially flow in the chamber as in the conventional design concept.

EXAMPLES

<First Example>

The above concept that the compressed fluid be promptly exhausted from the chamber finds its basis, as described above, in the finding that the compressed fluid remaining in the chamber acts as a resistance.

The dental air turbine handpiece A according to the first embodiment of the present invention will now be described with reference to FIGS. 1 to 3.

As illustrated in the drawings, the dental air turbine handpiece A according to the first embodiment of the present invention is composed of a head portion H, a grip portion G, and a neck portion N which is an end portion of the grip portion G and is connected continuously to the head portion H.

Figure 16:
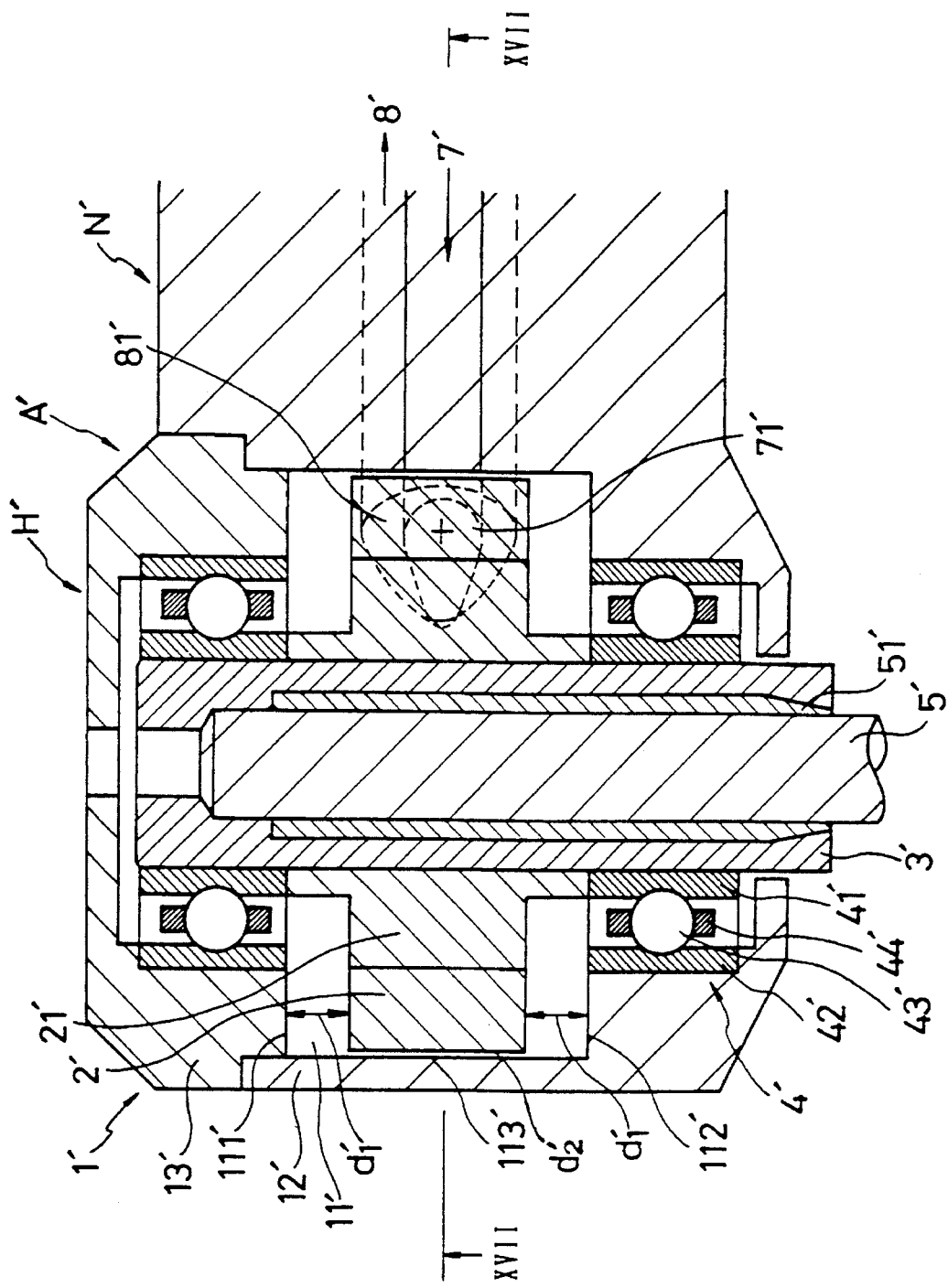
FIG. 16 is a fragmentary vertical cross-sectional view of a conventional medical (dental) air turbine handpiece.
Figure 17:
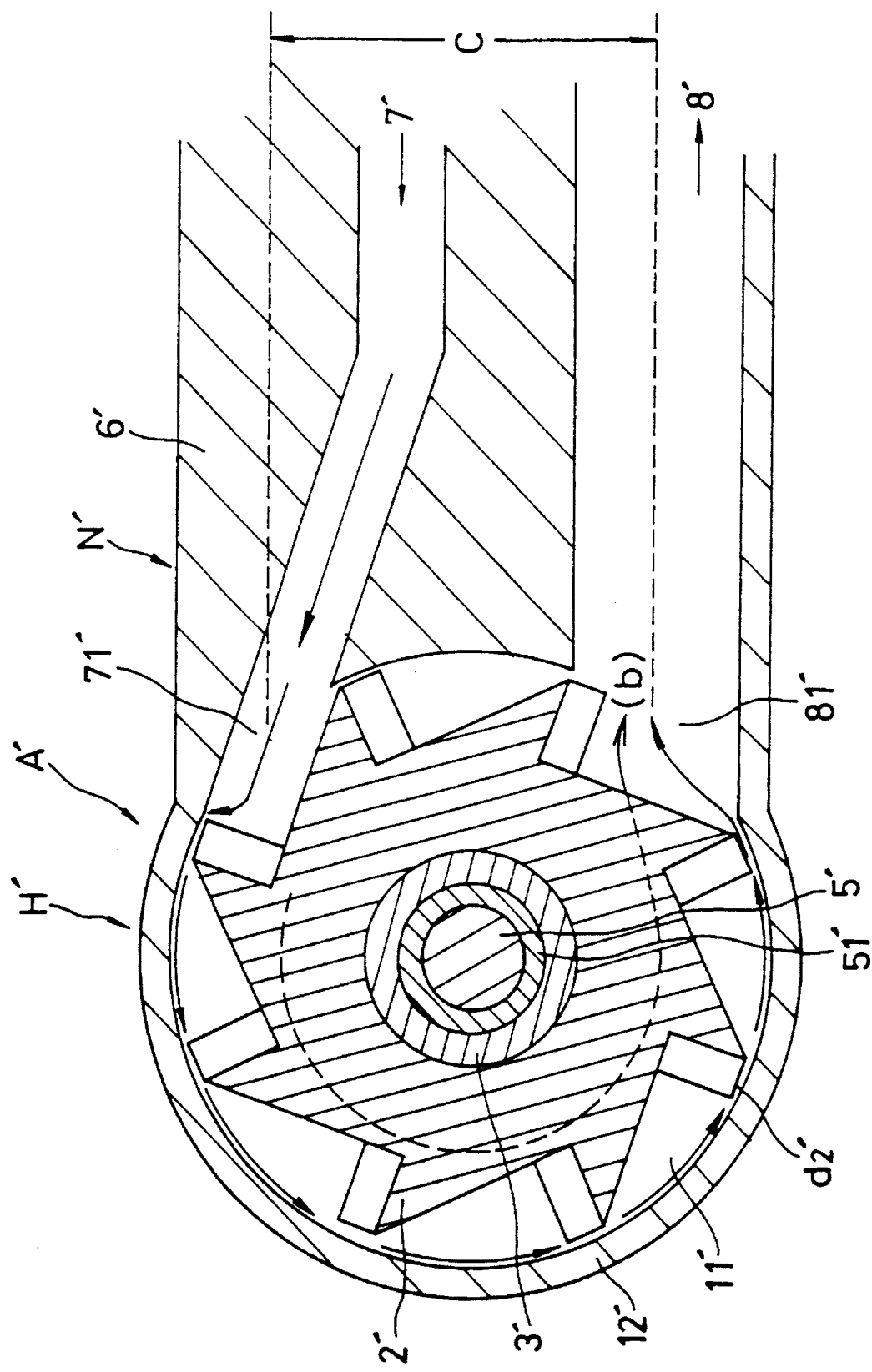
FIG. 17 is a cross-sectional view taken in the direction of arrows XVII—XVII of FIG. 16.
Figure 18:
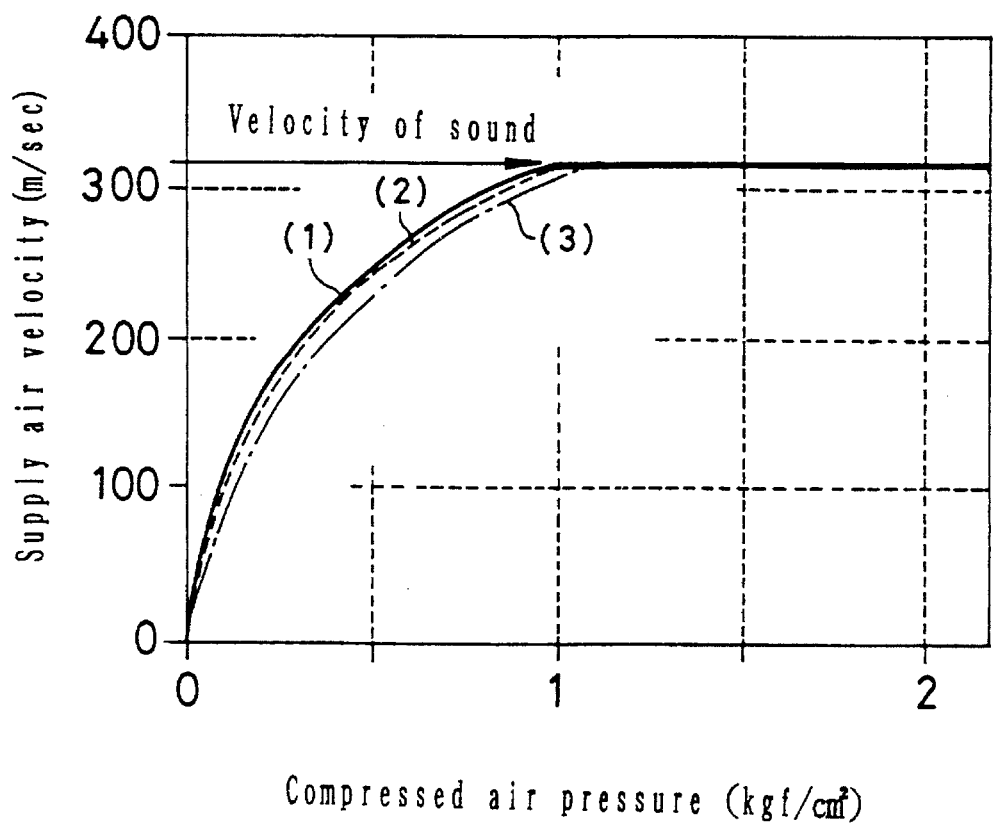
FIG. 18 is a graph showing a relationship (theoretical values) between supply air pressure and supply air velocity in an air turbine.
Figure 19:
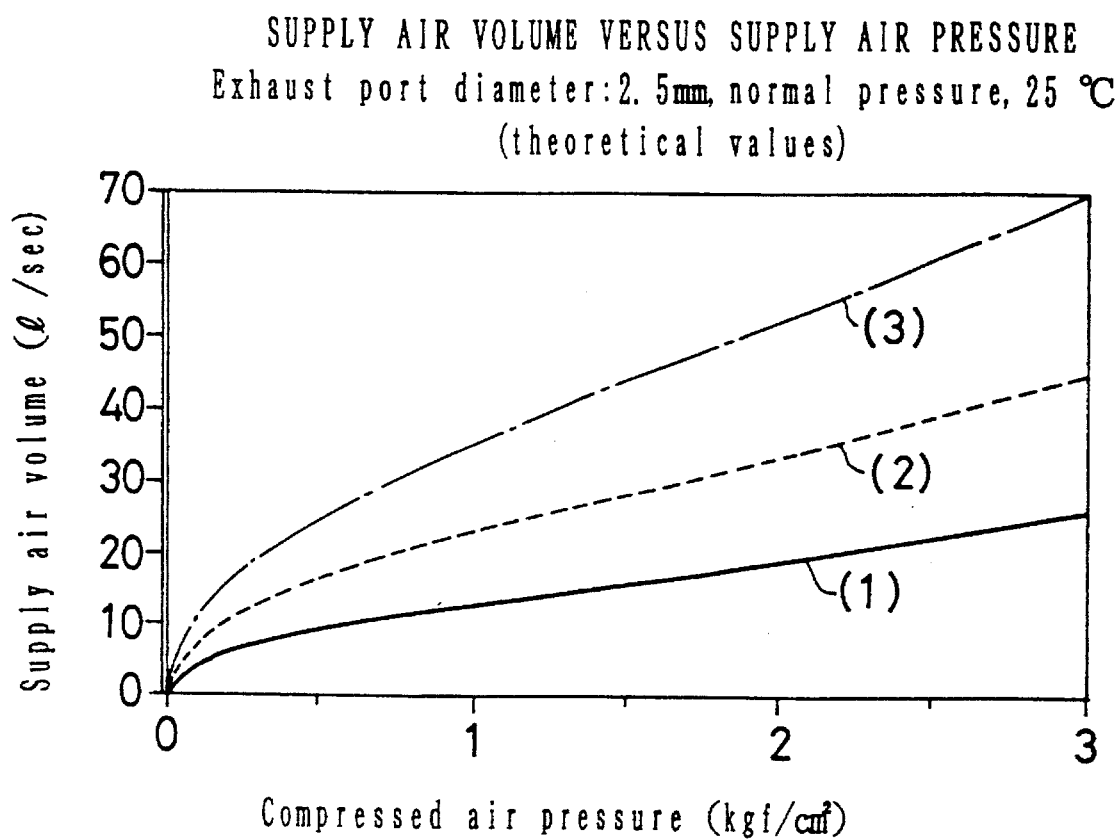
FIG. 19 is a graph depicting a relationship (theoretical values) of supply air pressure and supply (inducted) air volume in the air turbine.

Although the individual members (parts) of the conventional dental air turbine handpiece A' in FIGS. 16–17 have been referred to by primed reference numerals (1', 2', etc.), members (parts) which make up the dental air turbine handpiece A according to the first embodiment of the present invention will be referred to by reference numerals without the prime symbol (') in the subsequent description. As the like reference numerals indicate the like member (parts), their description is omitted herein.

Here, the manner of arrangement of an air supply port and an air exhaust port in the non-circumferential flow type, said manner of arrangement being the greatest characteristic feature of the present invention, will be described in detail.

Figure 2:
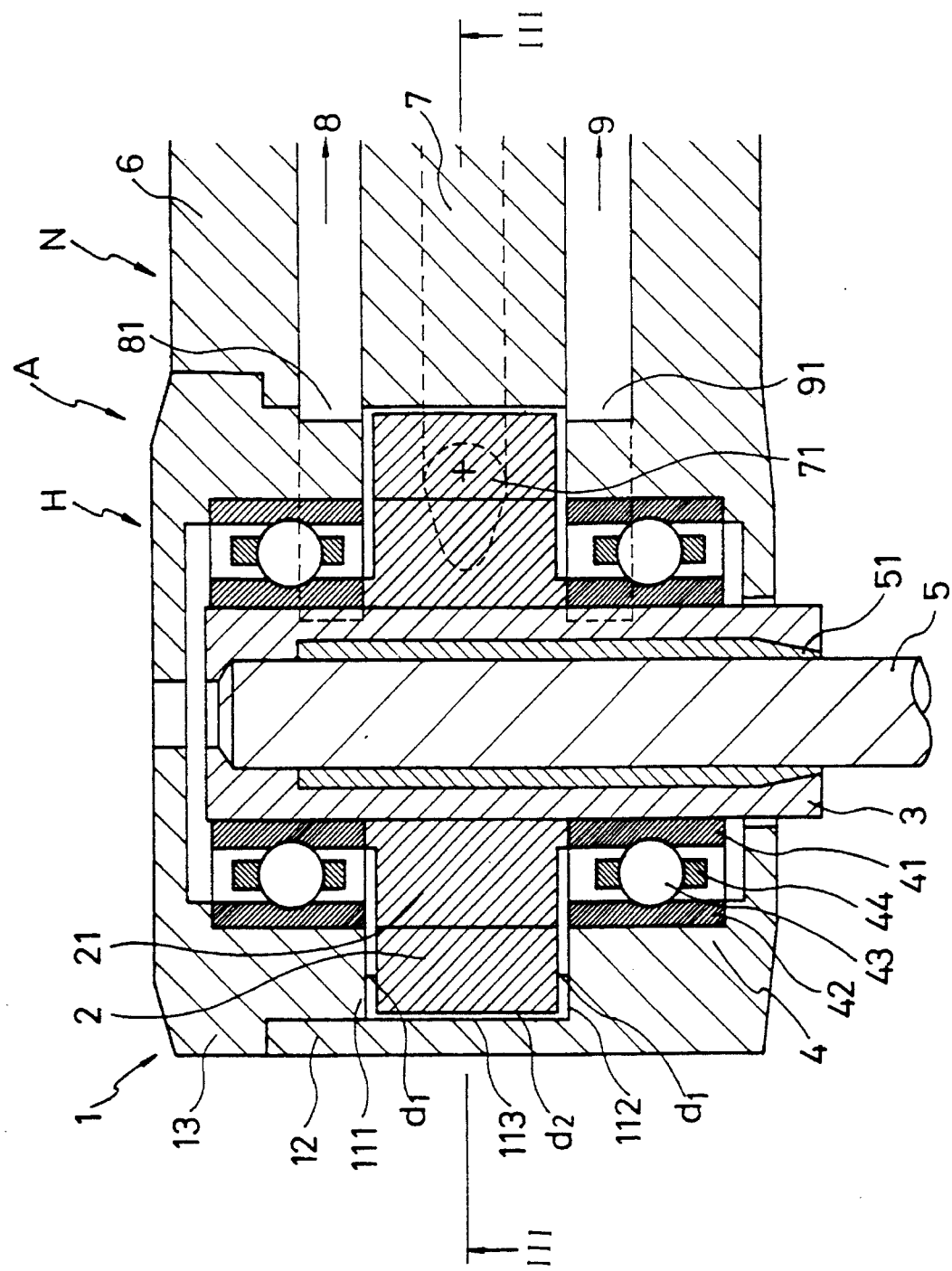
FIG. 2 is a fragmentary vertical cross-sectional view of a small (dental) air turbine handpiece according to a first embodiment of the present invention.

As is shown in FIGS. 2–3, an air supply channel 7 provided with a single air supply port 71 is arranged inside a main body 6 of the neck portion N so that compressed air can be injected against substantially central parts, as viewed in an axial direction, of turbine blades 2 disposed within a chamber 11 of a head 1.

The term "the axial direction of the turbine blades 2" as used herein means the direction which coincides with the direction of an axis of a turbine rotor shaft 3. Needless to say, the position of arrangement of the air supply port 71 should be determined so that the injected compressed air can transmit largest energy to each turbine blade 2 rotating within the chamber 11.

On the other hand, to permit prompt exhaustion of the compressed air from the chamber 11 immediately after causing the compressed air to collide against the turbine blades 2, two air exhaust ports 81,91 are arranged in total, one right above the single air supply port 71 and the other right below the same, both inside the main body 6 of the neck portion N as depicted in FIGS. 2 and 3.

To permit prompt exhaustion of compressed air from the interior of the chamber 11 immediately after collision of the compressed air against the turbine blades 2, the present invention requires arrangement of the exhaust ports at positions proximal to the air supply port. Incidentally, the above-described manner of arrangement of the air supply port and the air exhaust ports is one embodiment of the present invention. It is to be noted that the present invention is not limited to the embodiment.

Where the air exhaust ports 81,91 are arranged at the positions proximal to the air supply port 71 as described above, compressed air is formed into a compressed air stream a indicated by a solid arrow immediately after its collision against one of the turbine blades 2 irrespective of the speed of the turbine rotor shaft 3 as illustrated in FIG. 3.

This compressed air stream a is totally different from the compressed air stream b of the conventional circumferential type shown in FIG. 17.

To actually produce the above-described compressed air stream a in the dental air turbine handpiece A according to the first embodiment of the present invention, the following requirements are essential for the above-described embodiment:

(i) The air supply channel 7 has the single air supply port 71, and (ii) An arranged positional relationship between the single supply port 71 and the air exhaust ports 81,91 of the air exhaust channel 8 is set so that the air exhaust ports 81,91 are arranged at positions proximal to the supply port 71.

The above requirement (i) is obviously needed from a dimensional reduction of an equipment, economy (cost merit upon manufacture of equipments) and durability (the strength-related requirement of the neck portion).

Further, to ensure the materialization of the compressed air stream a, it is also important to reduce the interval ($d_1'$) between the turbine blades arranged in the chamber and each of the upper and lower walls of the chamber described with reference to FIG. 16 (prior art) and in connection with the embodiment of the present invention, the interval ($d_1$) in FIG. 2.

To allow prompt exhaustion of compressed air from the chamber 11 without causing it to circumferentially flow in the chamber 11 subsequent to its collision against the turbine blade 2, the spatial volume of the chamber 11 is preferably the same as the size of the turbine blades 2 arranged inside the chamber 11.

When the spatial volume of the chamber 11 and the size of the turbine blades 2 are substantially the same to assure rotation of the turbine blades 2, the compressed air inside the chamber 11 has higher probability of formation of a non-circumferential flow (a in FIG. 3) rather than the formation of a circumferential flow (b in FIG. 17) so that the compressed air is promptly exhausted through the exhaust port.

To make the spatial volume of the chamber 11 substantially the same as the size of the turbine blades 2 as described above means to set small the interval ($d_1$), namely, the interval ($d_1$) between each of upper and lower, inner walls 111,112 of the chamber 11 and the turbine blades 2 disposed within the chamber 11 as shown in FIG. 2.

The interval ($d_1$) has to be set so that the compressed air inside the chamber 11 forms a non-circumferential flow without formation of a circumferential flow or the probability of formation of such a non-circumferential flow becomes high.

The above-described interval $d_1$ can be set in accordance with various standards.

When the height (h) of the turbine blades (2) as viewed in the direction of the axis of the turbine rotor shaft 3 is used as a standard, for example, (see FIG. 4 to be described subsequently), it is only necessary to set the interval ($d_1$) at a value not greater than 1/10 of the height (h). Incidentally, conventional products are known to include those having 2.8 mm as the height (h).

When the interval ($d_2$) between the turbine blades (2) and a peripheral inner side wall 113 of the chamber 11 as viewed in a direction perpendicular to the direction of the axis of the turbine rotor shaft 3 is used as a standard (see FIG. 2), it is only necessary to set the interval ($d_1$) at a value not greater than 2.5 times the above interval ($d_2$). Incidentally, the conventional products are known to include those having 100–200 μm as the interval ($d_2'$) corresponding to the interval ($d_2$) (see FIG. 16). For example, dental air turbine handpieces ("JET MASTER FAR-E2") manufactured by J. MORITA MFG. CORP. include those having 100 μm as the interval ($d_2'$).

Describing further the value of the interval ($d_1$) in terms of an absolute value instead of a value relative to the height (h) or the interval ($d_2$), the interval ($d_1'$) of the conventional dental air turbine handpiece is extremely large, namely, 1150 μm (see FIG. 16). It is however preferred to set the value of the interval ($d_1$) at a value capable of giving high probability of formation of a non-circumferential flow, i.e., at 500 μm or smaller, with a value of 200–100 μm being more preferred.

As the value of the interval ($d_1$), it is preferred to set it as small as possible. This however results in the requirement for high accuracy on the members (parts). An interval ($d_1$) not greater than 500 μm can produce sufficient effects.

As will be indicated by experimental data to be described subsequently herein, the present invention cannot bring about any effects if the above interval ($d_1$) is set equal to the interval ($d_1'$) of the conventional product, that is, 1150 μm or even the interval ($d_1$) is reduced form 1150 μm to 600 μm. It is therefore surprising that excellent effects are produced in the range not greater than 500 μm.

In the dental air turbine handpiece A according to the first embodiment of the present invention, the size of the single air supply port 71 is as small as 50% or less of the height (h) of the turbine blades 2 (see FIG. 4) although it has relevance to the size of each air exhaust port.

Described more specifically, as will be indicated by the experimental data to be described subsequently herein, the size of the air supply port 71 can be, for example, 0.60–1.50 mm (absolute value) relative to the height (h=2.8 mm) of the turbine blades 2.

As the above-described size of the air supply port 71, the size (height or diameter) of the air supply port as viewed in an axial direction of the turbine blades (i.e., the direction of the axis of the turbine rotor shaft) is used as a standard for comparison.

In the dental air turbine handpiece A according to the first embodiment of the present invention, the manner of arrangement of the air supply channel 7 can be determined as desired.

Under the condition that the single air supply port 71 is provided, the air supply channel 7 is not limited to the single channel shown in FIGS. 2–3 but needless to say, can be formed of plural channels, although the manner of construction of the air supply channel has relevance to the thickness and strength of the main body 6 of the neck portion N.

In the dental air turbine handpiece A according to the first embodiment of the present invention, the total size of the air exhaust ports 81,91 arranged at the positions proximal to the air supply port 71 is preferably greater than the size of the air supply port 71 from the viewpoint of the efficiency of exhaustion.

As will be indicated by the experimental data to be described subsequently herein, the size of each of the air exhaust port can be, for example, 1.0 mm (absolute value) relative to the height (h=2.8 mm) of the turbine blades 2 although it has relevance to the size of the air supply port 71.

As the above-described size of each of the air exhaust ports 81,91, the size (height or diameter) of each air supply port as viewed in the axial direction of the turbine blades (i.e., the direction of the axis of the turbine rotor shaft) is used as a standard for comparison.

In the dental air turbine handpiece A according to the first embodiment of the present invention, no particular limitation is imposed on the cross-sectional shapes of the air supply port 71 and the air exhaust ports 81,91. For example, they can obviously be circular or rectangular in cross-section.

Further, the air supply channel 7 communicated to the single air supply port 71 and the air exhaust channels 8,9 communicated to the air exhaust ports 81,91, respectively, can be arranged as desired while taking into consideration the shape of the turbine blades 2 (including the number of the turbine blades), the strength of the neck main body 6 and the like. Although differences are observed, for example, between the manner of arrangement of the air supply channel and the air exhaust channel in FIG. 3 and those to be described subsequently herein, these channels are not limited to them but can be arranged as desired.

To exhaust compressed air from the chamber 11 of the head 1 as promptly as possible subsequent to its collision against the turbine blades in the medical air turbine handpiece A according to the present invention, it is important to adopt, for the supply and exhaust system of compressed air, the design concept which is totally different from the conventional design concept as described above. In relation to this, it is also preferred to use as the turbine blades those having a shape capable of promoting exhaustion of air.

FIGS. 4A and 4B through FIGS. 7A and 7B illustrate blades of various shapes. In each of these drawings, numeral 21 indicates a blade support on which the turbine blades 2 are fixedly mounted. In the individual drawings, those identified by A are fragmentary cross-sectional views whereas those designated by B are top plan views of the blades.

Figure 7A:
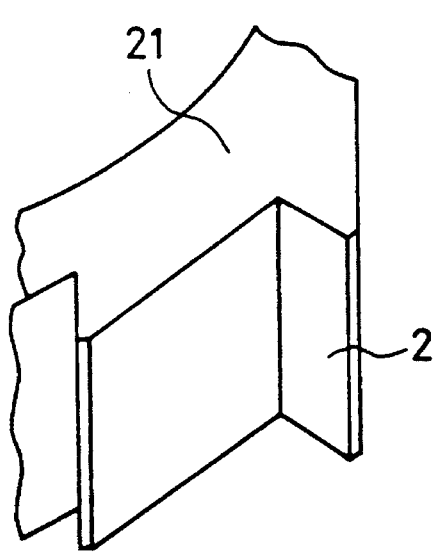
FIGS. 7A and 7B illustrate a fourth example of turbine blades employed in the small (dental) air turbine handpiece according to the present invention.
Figure 7B:

In each of the blades of FIG. 4A to FIG. 7B, a surface against which compressed air collides is formed as one or two arcuate surfaces so that the air can be guided to the air exhaust port along the arcuate surface or surfaces. Needless to say, the present invention is not limited to blades having such arcuate surfaces or surfaces and can use blades having a planar surface as shown in FIG. 7. Further, no limitation is imposed on the number of blades to be used.

In the dental air turbine handpiece A according to the present invention, the manner of supply and exhaustion of compressed air is not limited to that of the above-described first embodiment.

Namely, the manner of supply and exhaustion of compressed air is not limited to the embodiment that as shown in FIGS. 2 and 3, compressed air is injected from the air supply port 71 against substantially the central part of the turbine blade 2, is caused to promptly take a U-turn in both upward and downward directions of the turbine blade 2, and the air flows which have taken the U-turn are then exhausted through the two air exhaust ports 81,91 arranged separately right above and right below the air supply port.

Obviously, compressed air can be biased toward and injected against upper or lower parts of turbine blades and its exhaustion can be effected from the side of the parts toward which the compressed air are biased.

As the manner of arrangement of the air exhaust ports at positions proximal to the air supply port, the air exhaust ports can be arranged right above and/or right below (as viewed in the direction of the axis of the turbine rotor shaft 3 (i.e., at positions proximal to the air supply port as viewed in a vertical direction) or at positions proximal as viewed in horizontal directions, or these positions can be combined together.

Data of First Example and Comparative Examples

<Apparatuses>

To demonstrate the superiority of the type of the present invention to the conventional type, experiments will next be described.

A description Will first be made of the experimental models which were fabricated to facilitate collection and direct comparison of various experimental data and faithfully reflect the type of the present invention and the conventional type.

Figure 8:
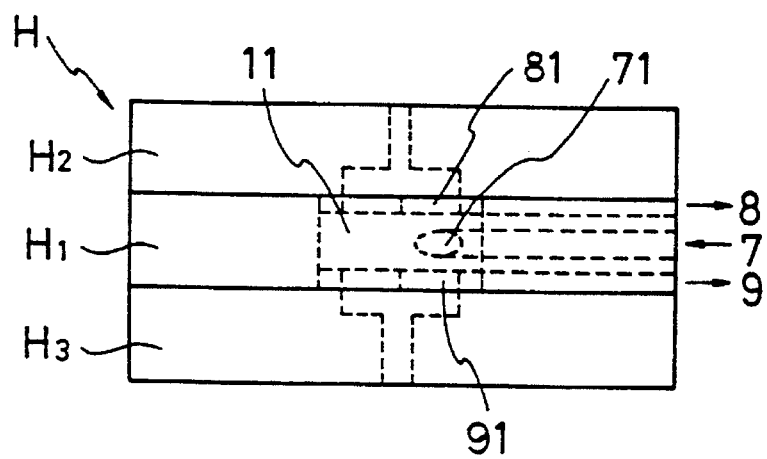
FIG. 8 is a side view of an experimental model equivalent to a small air handpiece of the same type as the present invention, in which some parts are illustrated see-through to indicate an air supply and exhaust system.
Figures 9A, 9B:
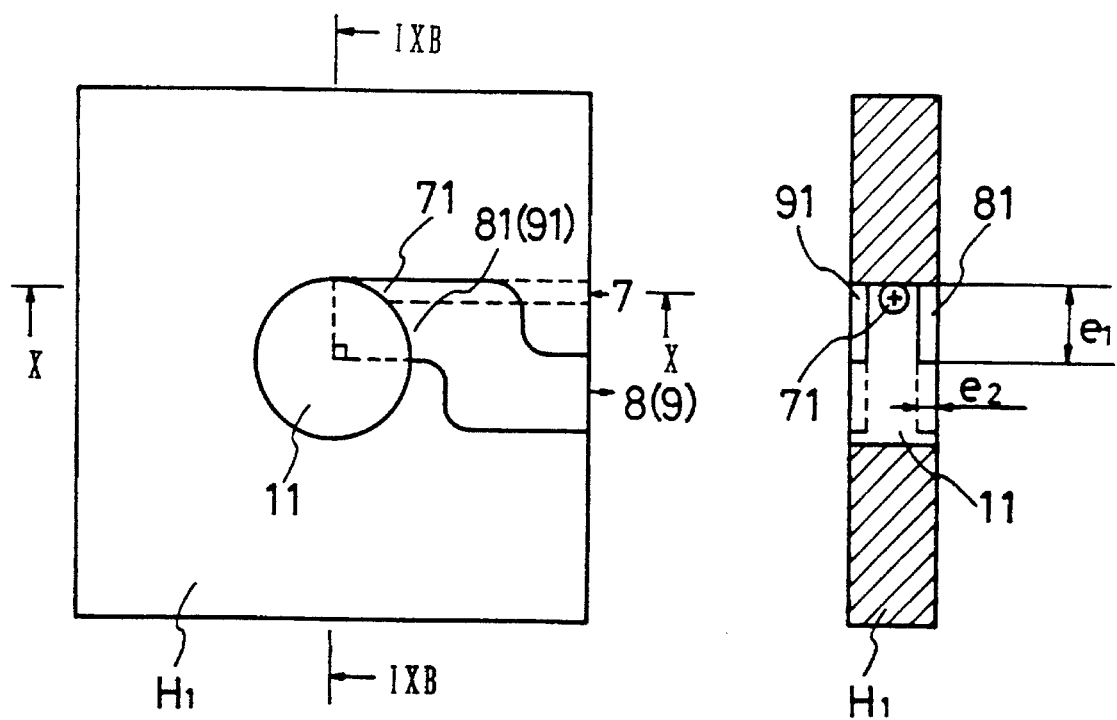
FIG. 9A is a plan view of a housing member $H_1$ in FIG. 8.
FIG. 9B is a cross-sectional view taken in the direction of arrows IXB—IXB of FIG. 9A.
Figure 10:
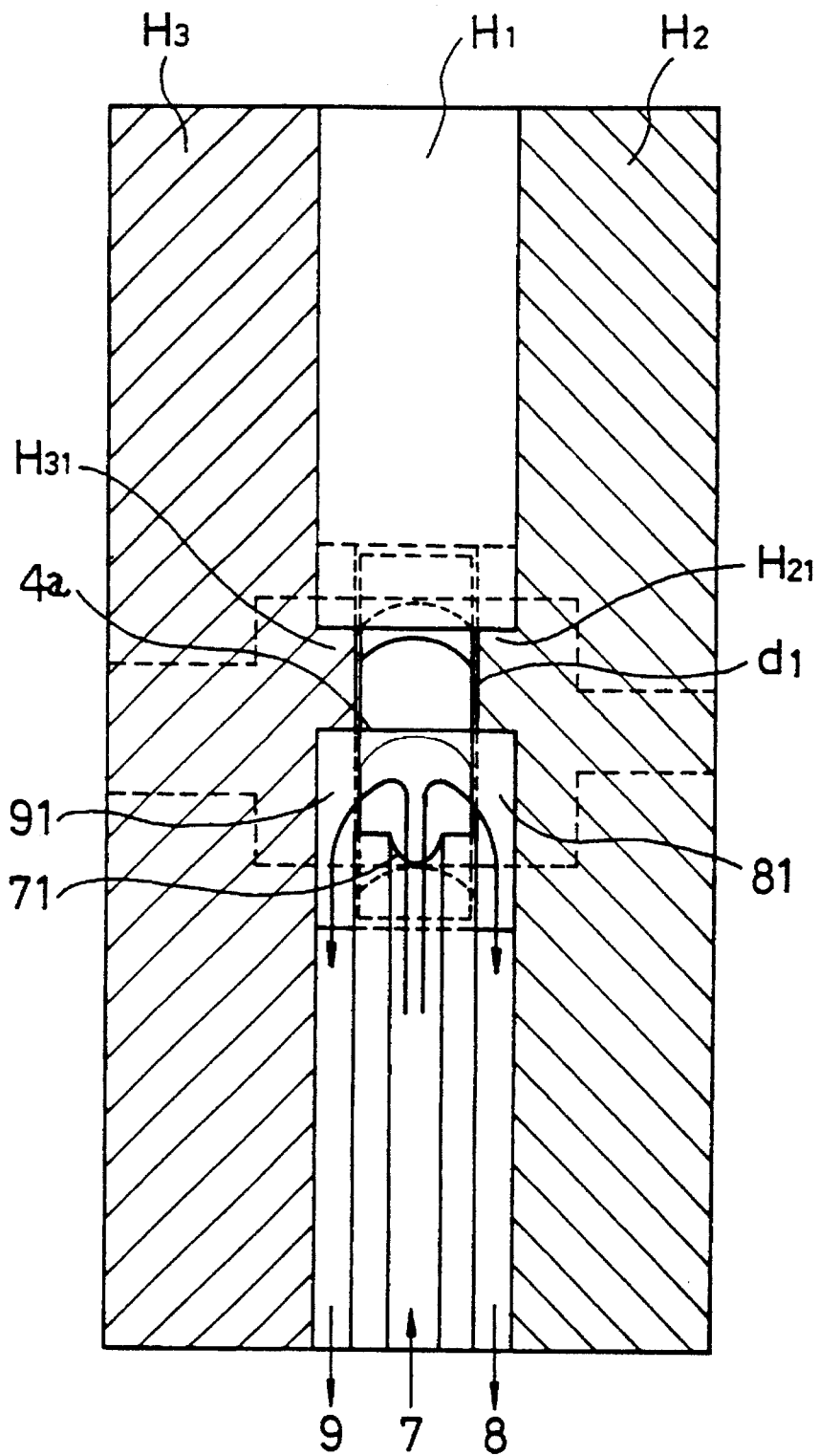
FIG. 10 is a cross-sectional view taken in the direction of an axis of an air supply channel 7, that is, in the direction of arrows X—X of FIG. 9A.

The experimental model of the invention type faithfully reflects the structure described above with reference to FIGS. 2–3 and is shown in FIGS. 8 to 10.

Figure 11:
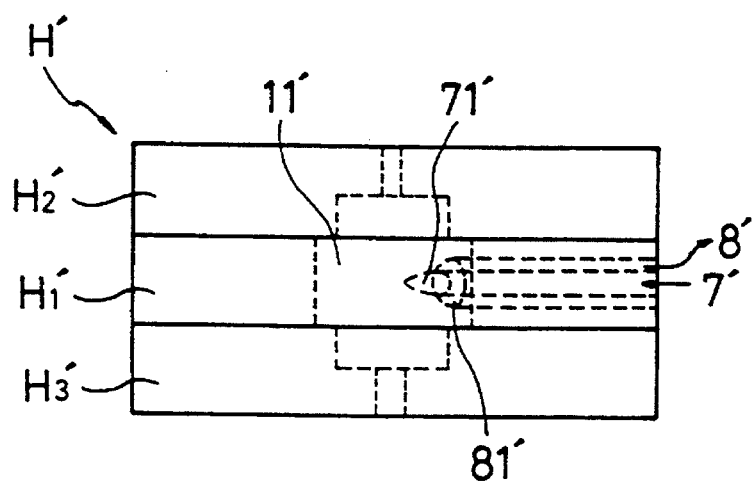
FIG. 11 is a side view of an experimental model equivalent to a small air handpiece of the same type as the conventional art, in which some parts are illustrated see-through to indicate an air supply and exhaust system.
Figures 12A, 12B:
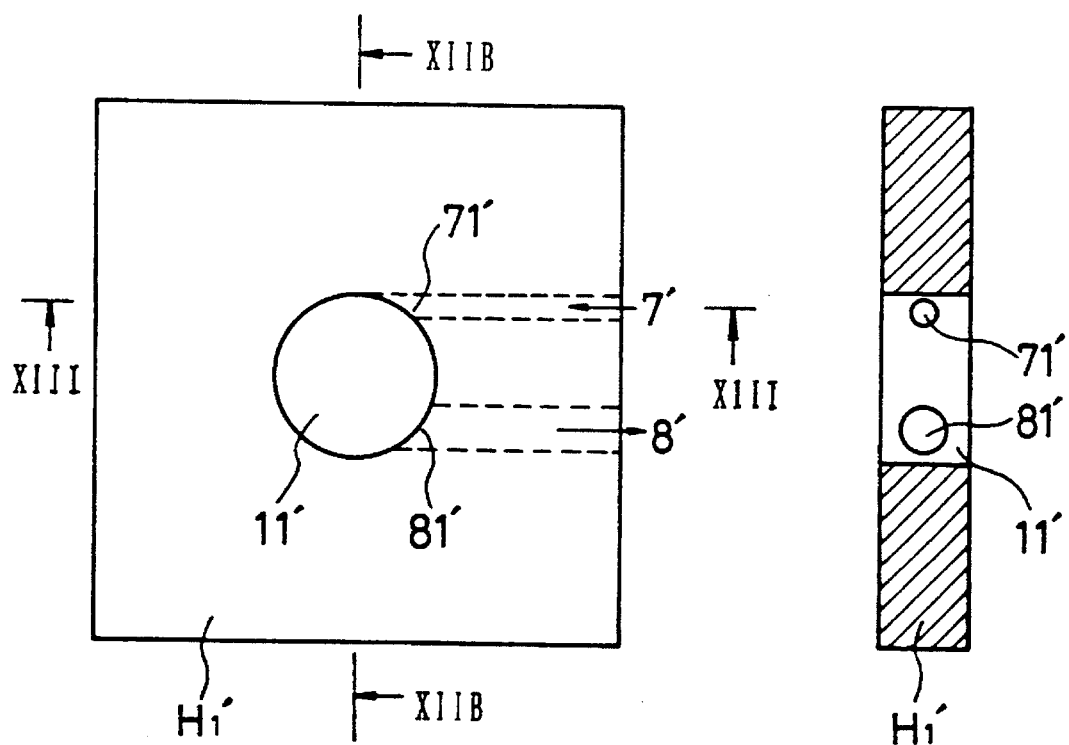
FIG. 12A is a plan view of a housing member $H_1$ in FIG. 11.
FIG. 12B is a cross-sectional view taken in the direction of arrows XIIB—XIIB of FIG. 12A.
Figure 13:
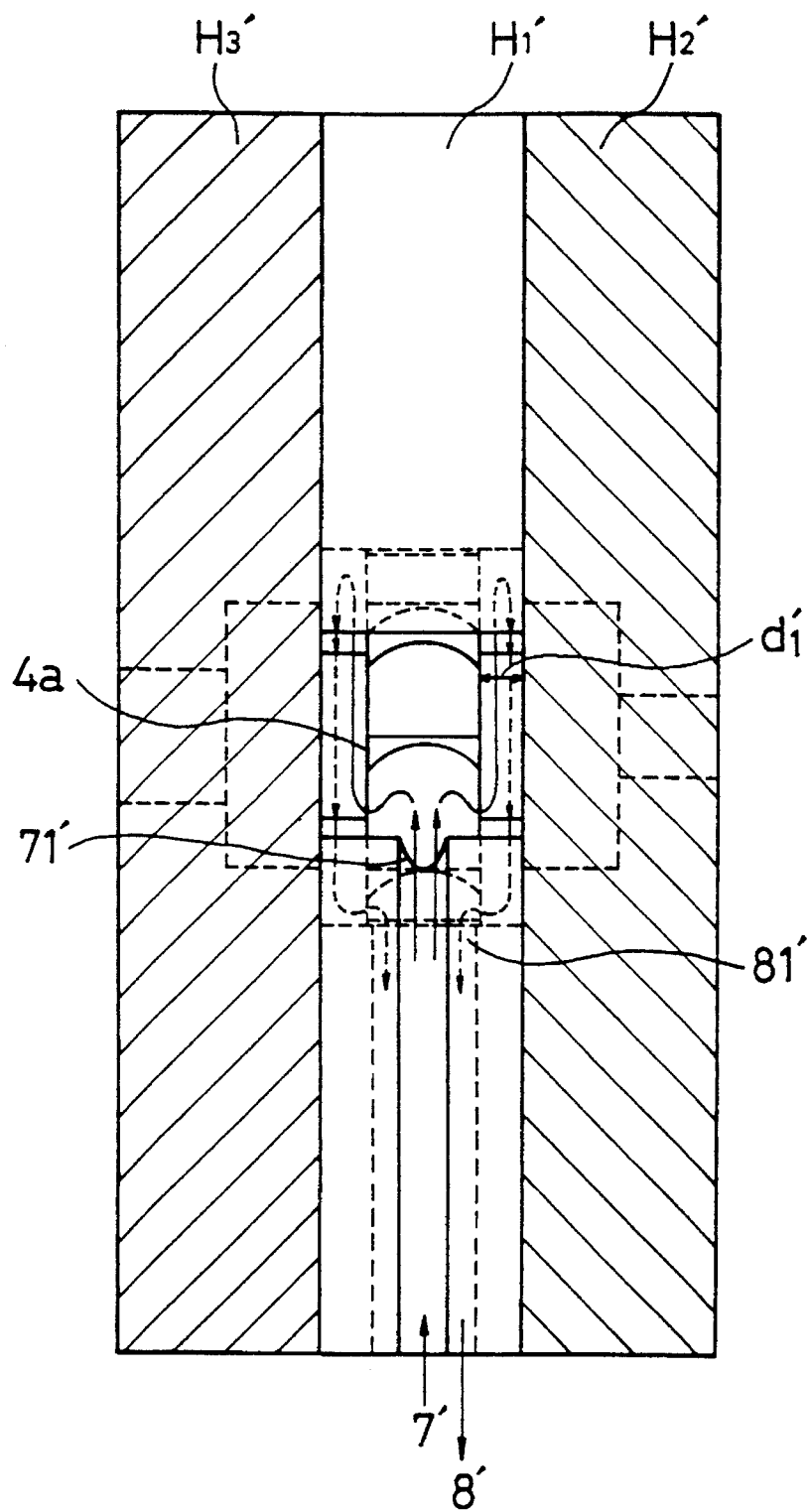
FIG. 13 is a cross-sectional view taken in the direction of an axis of an air supply channel 7', that is, in the direction of arrows XIII—XIII of FIG. 12A.

The experimental model of the conventional type faithfully reflects the structure described above with reference to FIGS. 16 and 17 and is depicted in FIGS. 11 to 13.

(1) The experimental model of the invention type:
(1)-(i) Outline of the experimental model of the type according to the present invention The outline of the experimental model of the invention type is illustrated in FIG. 8.

Indicated at letter H in FIG. 8 is a head portion whose housing members are constructed of three transparent synthetic resin (acrylic resin) plates $H_1, H_2, H_3$. An supply channel 7 and exhaust channels 8,9 for compressed air were formed in the central synthetic resin plate $H_1$ as shown in the drawing. Needless to say, bearings are accommodated in internal cavities indicated by dashed lines in the housing members $H_2, H_3$. The synthetic resin was used to form the housing members, because the synthetic resin is suitable in setting various experimental conditions (for example, the sizes, shapes and the like of the supply and exhaust ports).

FIG. 9A is a plan view of the housing member $H_1$ whereas FIG. 9B is a cross-sectional view taken in the direction of arrows IXB—IXB of FIG. 9A. The manner of arrangement of the air supply channel 9 and the air exhaust channels 8,9 are illustrated in these drawings.

FIG. 10 is a cross-sectional view of the experimental model of FIG. 9 with turbine blades arranged in a chamber 11, as viewed in the direction of an axis of the air supply channel 7. Namely, FIG. 10 is a cross-sectional view taken in the direction of arrows X—X of FIG. 9A. The other housing members $H_2, H_3$ are also shown to clearly indicate the flowing directions of streams of pressurized air. It is to be noted that hatching is omitted from the housing member $H_1$ to show other important elements.

Figure 4A:
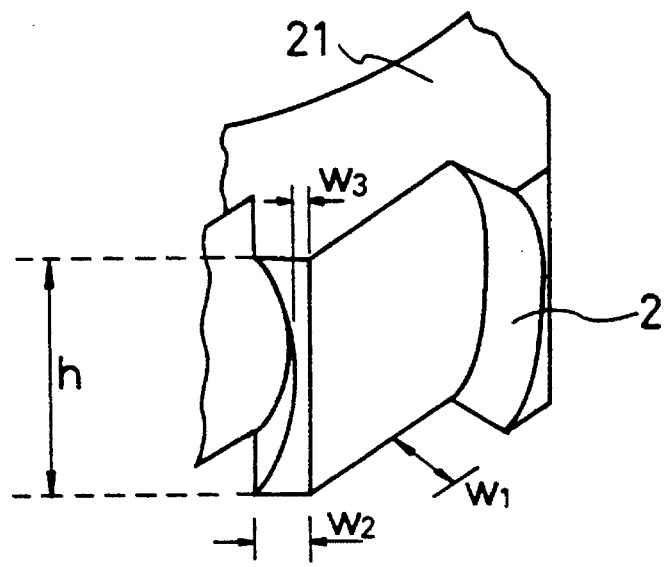
FIGS. 4A and 4B illustrate a first example of turbine blades employed in the small (dental) air turbine handpiece according to the present invention.
Figure 4B:
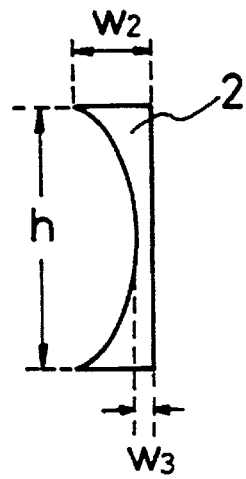
Figure 5A:
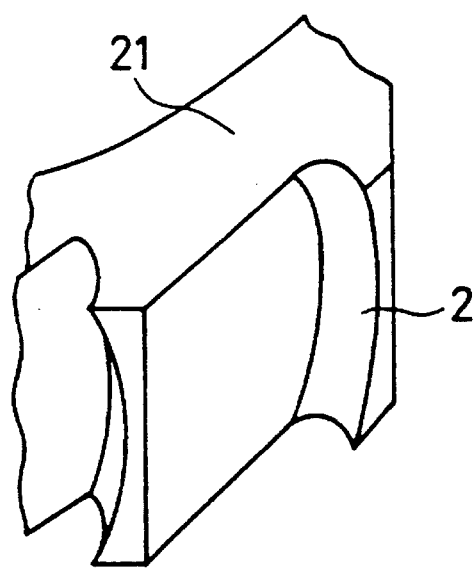
FIGS. 5A and 5B illustrate a second example of turbine blades employed in the small (dental) air turbine handpiece according to the present invention.
Figure 5B:
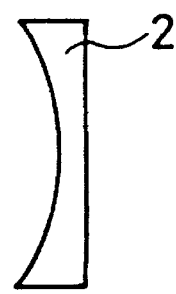
Figure 6A:
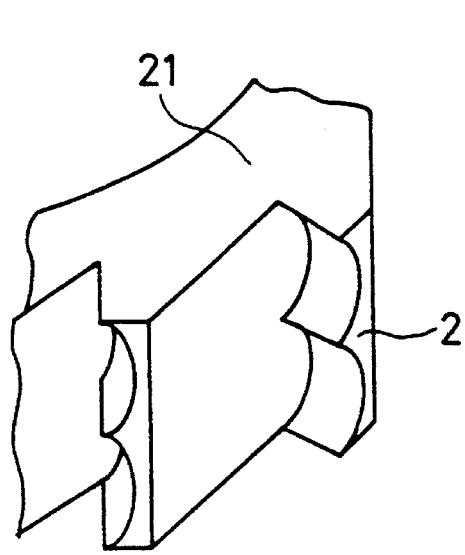
FIGS. 6A and 6B illustrate a third example of turbine blades employed in the small (dental) air turbine handpiece according to the present invention.
Figure 6B:

In the drawing, symbol $4a$ indicates that the turbine blades have the shape illustrated in FIG. 4A. On the other hand, $d_1$ indicates the interval between the turbine blades and each of the upper and lower housing members $H_2, H_3$.

As is understood from the foregoing, the head 1 of the head portion H and the main body 6 of the neck portion N in the small handpiece with the fluid driven turbine, according to the present invention, can be obviously made of a synthetic resin. In this case, it is preferred, needless to say, to choose a synthetic resin which has durability against heat and vibrations to be produced by the turbine system which rotates at high speeds.

Formation of the above-described parts with such a synthetic resin in the present invention makes it possible to provide a small handpiece with a fluid driven turbine which is superior in economy and weight reduction to conventional metal-made handpieces with a fluid driven turbine, to say nothing of ease in manufacture.

(1)-(ii) Experimental conditions for the experimental model of the invention type Experimental conditions for the above-described experimental model of the invention type are as follows:

<Experimental Conditions>

Pressure of compressed air supplied (the pressure of compressed air): 2.5 kgf/cm$^2$ Inner diameter of a head chamber 11: 9.1 mm Size and number of turbine blades (see FIGS. 4A and 4B): $w_1$=1.3 mm in FIG. 4A; h=2.8 mm, $w_2$=0.8 mm and $w_3$=0.13 mm in FIG. 4B. Eight blades were mounted on a turbine blade support 21.

Interval ($d_1$) between the housing members $H_2, H_3$ and the turbine blades and thickness of the housing member $H_1$:
$d_1$: Basically 150 μm, but values of 1150–600 μm were also adopted for comparison with the conventional type.
Thickness of $H_1$: 5.1 mm (Note) As the thickness of $H_1$ was 5.1 mm and the height (h) of the turbine blades was 2.8 mm, spaces of 1150 μm in width were formed both above and below the turbine blades (1150 μm×2=2.3 mm) when the turbine blades were arranged centrally with respect to the thickness of $H_1$.

Positions of arrangement of air supply and exhaust ports and their sizes:

Positions of arrangement of air supply and exhaust ports: See FIGS. 9A and 9B. Diameter of the air supply port 71 of the air supply channel 7: Varied in both directions with 1.2 mm as a central value (see Tables 1 and 2). Size ($e_1 \times e_2$) of the air exhaust ports 81,91 of the air exhaust channels 8,9: Varied in both directions with 4.55×1 mm as a central value (see Tables 1 and 2).

(2) The experimental model of the conventional type:
(2)-(i) Outline of the experimental model of the conventional type The outline of the experimental model of the conventional type is illustrated in FIGS. 11 to 13.

FIGS. 11 to 13 correspond to FIGS. 8 to 10 showing the experimental model of the invention type, so that their differences can be readily envisaged.

Particularly large differences are found in the manner of arrangement of the air supply channel (port) 7' (71') and the air exhaust channel (port) 8' (81') and also in that, as is illustrated in FIG. 13, the interval ($d_1'$) between the housing members $H_2',H_3'$ and the turbine blades 4a is large to permit circumferential flow of compressed air in the chamber 11'.

It is to be noted that in FIG. 13, hatching is omitted from the housing member $H_1'$ to show other important elements.
(1)-(ii) Experimental conditions for the experimental model of the conventional type Experimental conditions for the above-described experimental model of the conventional type are as follows:

<Experimental Conditions>

Compared with the experimental conditions for the experimental model of the invention type, exactly the same conditions were employed except for the following conditions:

Interval ($d_1'$) between the housing members $H_2',H_3'$ and the turbine blades:

$d_1'$: Basically 1150 μm, but the value of 150 μm was also adopted for comparison with the invention type.
(Note) The above described value of 1150 μm as $d_1'$ was borrowed from a conventional product. The thickness of the housing member $H_1'$ was the same as the corresponding thickness in the invention type.

Positions of arrangement of air supply and exhaust ports and their sizes: Positions of arrangement of air supply and exhaust ports: See FIGS. 12A and 12B. Diameter of the air supply port 71' of the air supply channel 7': 1.2 mm. Size ($e_1 \times e_2$) of the air exhaust port 81' of the air exhaust channel 8: Varied to 3.0 mm and 2.5 mm in diameter and also to 3.8×3.8 mm and 3.8×3.0 mm in $e_1 \times e_2$. Incidentally, the diameter of 1.2 mm as the size of the air supply port and the diameter of 2.5 mm as the size of the air exhaust port were borrowed from conventional products.

(3) An experimental model of the USP type:
Further, an experimental model with the construction, which is disclosed in U.S. Pat. Nos. 3,893,242 and 4,020,556 described above as conventional art, incorporated in the experimental model of the invention type (hereinafter called "the experimental model of the USP type") was also fabricated and experimented.

The experimental model of the USP type is an experimental model fabricated in view of the technical details disclosed in the above U.S. patents, especially their FIG. 2, FIG. 3 and FIG. 9 and further by taking into consideration the following matters:

In view of the feature that the size (diameter) of each of the two air supply ports is substantially the same as the height of the turbine blades, two air supply ports (1.2 mm in diameter×2) were arranged in the experimental model of the invention type so that the ratio of the sum of the diameters of the two air supply ports to the height (h) (h=2.8 mm) of the blades became larger. Further, the individual air supply ports were arranged to inject compressed air against adjacent ones of the blades, respectively. Incidentally, the percentage of the (total) size of the air supply port (s) relative to the blade height (h) was 43% (1.2/2.8) in the invention type and 86% (2.4/2.8) in the USP type.

The interval ($d_1'$) between each of the upper and lower, inner wall of the chamber and the turbine blades was set in the range of 1150–600 μm like the design concept of the conventional art.

In those experiments, maximum rotational speeds (X) and air volumes (Y) per unit time under a predetermined pressure (2.5 kgf/cm$^2$) of compressed supply air were measured using the various experimental models described above.

<Evaluation Standards>

Prior to presenting the results of the experiments, a description will now be made of evaluation standards for evaluating the results of the experiments.

Needless to say, the present inventors consider an excellent dental air turbine handpiece as one excellent in the torque (output) performance of a turbine rotor shaft.

Further, the present inventors also consider preferable to use the following evaluation standards in making the evaluation as to whether or not the torque (output) performance of the turbine rotor shaft is excellent:

(1) A maximum rotation speed of a preferred level can be realized by a supply (inducted) air volume per unit time. Needless to say, an increase in torque (an improvement in output) should desirably be such that the maximum rotational speed of the turbine rotor shaft becomes higher within a preferred range. Further, the maximum rotational speed of the turbine rotor should have a strong correlation with the supply (inducted) air volume per unit time. The present inventors therefore believes that the ratio of the maximum rotational speed (X) to the supply air volume (Y) per unit time, namely, the supply-air-volume-basis efficiency (X/Y) is a practical first evaluation standard. The present inventors believe the above-described evaluation standard to be practical, because the approach in which the supply air volume (Y) per unit time is progressively and substantially increased to make the maximum rotational speed (X) higher is evaluated low for the application of unduly large load on the air supply system, the indispensable modifications to an already-existing air supply system (i.e., the need for a large investment in new facilities due to lack of ability) and the like.

Obviously, the above-described first evaluation standard commonly bring about the advantages that an already-existing facility can be use as an air supply system for a dental air turbine handpiece having a high supply-air-volume-basis efficiency (X/Y), no high load is applied to the air supply system (a compressor or the like) and the noise of operations small.

(1) To have large cutting ability.
What should be kept in mind upon evaluation of experimental data in accordance with the above-described first evaluation standard is that a large value is indicated as the supply-air-volume-basis efficiency (X/Y) when the supply air volume (X) is small and a somewhat high rotational speed (Y) (but not of a preferred level) is achieved in the turbine system. This means that, even if a dental air turbine handpiece is evaluated as having good supply-air-volume-basis efficiency (X/Y) in accordance with the above-described first evaluation standard, the dental air turbine handpiece is inferior in cutting ability in view of its low-level rotational speed in cutting work which is its principal work. For the evaluation of performance in terms of a cut amount, the present inventors have therefore established, as a second evaluation standard, a standard by adding the maximum rotational speed (X), which shows a strong correlation with a cut amount, to the above-described first evaluation standard (X/Y), namely, the below-described cut-amount-basis efficiency weighted by the maximum rotational speed (X). The cut-amount-basis efficiency is represented by $(X) \cdot (X/Y) = X^2/Y$. Obviously, a dental air turbine handpiece evaluated to have a high cut-amount-basis efficiency $(X^2/Y)$ in accordance with the second evaluation standard produces less cutting vibrations and permits sophisticated dental treatment. Clinically, it has the advantage that patients can be kept free from unpleasant feeling or pain. Further, a further dimensional reduction in handpieces can be realized because it is possible to achieve the same performance as the conventional products even if a still smaller turbine rotor is employed.

Accordingly, the experimental results to be presented below must be fully analyzed based on:

(1) the supply-air-volume-basis efficiency (X/Y) as the first evaluation standard, and (2) the cut-amount-basis efficiency $(X^2/Y)$ as the second evaluation standard.

<Experimental Results and Discussion>

(1) Experimental Results

The results of the experiments conducted using the above-described experimental models are presented below in Tables 1 and 2. The experiment was conducted at room temperature. i.e., at 25° C.

In both the tables, the individual items have the following meanings:

(1) Invention type: Experiments by the above-described experimental model of the invention type are meant.

(2) Conventional type: Experiment by the above-described experimental model of the conventional type are meant.

(3) USP type: Experiments by the above-described experimental model reproduced from the type disclosed in U.S. Pat. Nos. 3,893,242 and 4,020,556 are meant. Namely, an experimental model of the invention type was provided with two air supply ports of the predetermined size to reproduce the apparatus disclosed in the above U.S. patents.

(4) Diameter of air supply port: The cross-sectional shape of the air supply port was circular (unit: mm). See FIG. 8.

(5) Size of air exhaust port(s) ($e_1.e_2$): The cross-sectional shape of the air exhaust port was rectangular (unit: $mm^2$). End ($e_1$)×side ($e_2$). See FIGS. 9A and 9B.

(6) Diameter of air exhaust port(s): The cross-sectional shape of each air exhaust port was circular (unit: $mm^2$). See FIGS. 12A and 12B.

(7) $d_1$: The interval between the inner wall of the chamber and the turbine blades in the model of the invention type (see FIG. 10). $d_1$=150 μm.

(8) $d_1'$: The interval between the inner wall of the chamber and the turbine blades in the model of the conventional type (see FIG. 13). $d_1'$=1150–600 μm.

(9) Maximum speed (X): The maximum rotation speed of the turbine system when air was supplied at a constant elevated pressure (2.5 kgf/cm²) (unit: $10^4$ rpm).

(10) Supply air volume (Y): The volume of air supplied to (inducted in) the turbine system. Converted to the value at normal pressure and 25° C. (unit: l/min).

(11) X/Y: The first evaluation standard (supply-air-volume-basis efficiency).

(12) X.XY: The second evaluation standard (cut-amount-basis efficiency).

(13) The above-described pressure of the supplied air was measured by a digital pressure sensor and is presented with the unit (kgf/cm²).

(14) The above maximum speed (X) was measured by counting signals from a photoelectric switch of the high-speed response type by a counter (a counter per unit time) and is presented with the unit ($10^4$ rpm).

(15) The above supply air volume (Y) was measured by a thermal mass flow rate sensor and is presented by a value converted to normal pressure and 25° C.

TABLE 1

| Experiment No. | | | Invention type | | | | Conventional type | | | |
| --- | --- | --- | --- | --- | --- | --- | --- | --- | --- | --- |
| | | | 1 | 2 | 3 | 4 | 5 | 6 | 7 | 8 |
| Diameter of air supply port | | | 1.2 mm | 1.2 mm | 1.2 mm | 1.2 mm | 1.2 mm | 1.2 mm | 1.2 mm | 1.2 mm |
| Size of air exhaust port(s) ($e_1 \cdot e_2$) | | | 9.1 · 1 (two ports) | 4.55 · 1 (two ports) | 4.0 · 1 (two ports) | 2.3 · 1 (two ports) | 3.8 · 3.8 | 3.8 · 3.0 | — | — |
| (diameter) | | | — | — | — | — | — | — | 3.0 | 2.5 |
| 8 $d_1$] Invention range | Max. speed | (X) | 45.0 | 47.5 | 49.0 | 37.0 | — | — | 37.6 | 37.6 |
| | Supply air volume (Y) | | 42.0 | 39.0 | 38.5 | 37.0 | — | — | 40.5 | 40.5 |
| | X/Y | | 1.07 | 1.22 | 1.27 | 1.00 | — | — | 0.93 | 0.93 |
| | X · X/Y | | 48.2 | 58.0 | 62.2 | 37.0 | — | — | 34.9 | 34.9 |
| [$d_1'$] Convention product range | Max. speed | (X) | 41.9 | 41.3 | — | — | 41.6 | 41.8 | 42.4 | 42.0 |
| | Supply air volume (Y) | | 45.5 | 39.0 | — | — | 45.0 | 43.7 | 40.3 | 39.6 |
| | X/Y | | 0.92 | 1.06 | — | — | 0.92 | 0.96 | 1.05 | 1.06 |
| | X · X/Y | | 38.6 | 43.7 | — | — | 38.4 | 40.0 | 44.6 | 44.5 |

TABLE 2

| Experiment No. | | Invention type | | | | USP type | | | | | |
|---|---|---|---|---|---|---|---|---|---|---|---|
| | | 9 | 10 | 11 | 12 | 13 | 14 | 15 | 16 | 17 | 18 |
| Diameter of air supply port | | 0.60 (one port) | 0.90 (one port) | 1.20 (one port) | 1.50 (one port) | 1.20 (two ports) | 1.20 (two ports) | 1.20 (two ports) | 1.20 (two ports) | 1.20 (two ports) | 1.20 (two ports) |
| size of air exhaust ports ($e_1 \cdot e_2$) (Two ports were arranged.) | | 4.55 · 1 | 4.55 · 1 | 4.55 · 1 | 4.55 · 1 | 4.55 · 1 | 4.55 · 1 | 4.55 · 1 | 9.1 · 1 | 4.0 · 1 | 2.3 · 1 |
| Pressure of supplied air | | 2.5 | 2.5 | 2.5 | 2.5 | 2.5 | 1.0 | 0.75 | 1.0 | 1.0 | 1.0 |
| [$d_1$] Invention range | Max. speed (X) | 19.0 | 42.4 | 47.5 | 51.0 | — | — | — | — | — | — |
| | Supply air volume (Y) | 10.0 | 22.6 | 39.0 | 58.5 | — | — | — | — | — | — |
| | X/Y | 1.90 | 1.88 | 1.22 | 0.87 | — | — | — | — | — | — |
| | X · X/Y | 36.1 | 79.7 | 58.0 | 44.5 | — | — | — | — | — | — |
| [$d'_1$] Convention product range | Max. speed (X) | 12.7 | 27.6 | 41.3 | 42.5 | 51.8 | 44.9 | 40.3 | 45.1 | 45.6 | 37.3 |
| | Supply air volume (Y) | 10.5 | 23.0 | 39.0 | 60.0 | 71.0 | 44.5 | 38.0 | 49.0 | 43.9 | 42.4 |
| | X/Y | 1.21 | 1.20 | 1.06 | 0.71 | 0.73 | 1.01 | 1.06 | 0.92 | 1.04 | 0.88 |
| | X · X/Y | 15.4 | 33.5 | 43.7 | 30.1 | 37.8 | 45.3 | 42.7 | 41.5 | 47.4 | 32.8 |

(2) Discussion on the Experimental Results (i) Discussion on the Experimental Results (Table 1)

Table 1 presents the experimental results of the invention type (Experiment Nos. 1–4) and of the conventional type (Experiment Nos. 5–8).

Namely, Table 1 shows the results of the experiments, in which an investigation was conducted to determine how characteristics would change in both the types when the size and position(s) of the air exhaust port(s) and the values of the intervals ($d_1, d_1'$) were changed while maintaining the pressure of supplied compressed air and the diameter and cross-sectional area of the air supply port constant at 2.5 kgf/cm$^2$ and at 1.2 mm and 1.13 mm$^2$, respectively.

As is clearly envisaged from Table 1, the model of the invention type was found to exhibit superior effects in both the first evaluation standard (X/Y) and the second evaluation standard (X.X/Y) to the model of the conventional type.

The data under the columns of Experiment No. 1 and No. 2 and the row of $d_1'$ are data obtained when in the model of the invention type, $d_1$ was changed from 150 μm to $d_1'$ (1150–600 μm), namely, only the value ($d_1$) was brought close to the conventional design concept. In this case, the characteristic values were substantially deteriorated, thereby indicating that the present type and the conventional type are totally different in design concept and advantageous effects.

On the other hand, the data under the columns of Experiment No. 7 and No. 8 and the row of $d_1$ are data obtained when in the experimental model of the conventional type, $d_1'$ was changed from 1150–600 μm to $d_1$ (150 μm), namely, only the value ($d_1'$) was brought close to the design concept of the present application. Here again, the characteristic values were significantly deteriorated like the above-described experiments, thereby indicating that the present type and the conventional type are totally different in design concept and advantageous effects.

(ii) Discussion on the Experiment Results (Table 2)

Table 2 presents the experimental results of the invention type (Experiment Nos. 9–12, among which Experiment No. 11 is the same as Experiment No. 2 described above) and of the USP type (Experiment Nos. 13–16).

Namely, Table 2 shows the results of the experiments, in which an investigation was conducted to determine how characteristics would change in both the types when the size of the single air supply port in the present type was changed (to permit a comparison with the USP type having two air supply ports of 1.2 mm in diameter as described above) wile maintaining the pressure of supplied compressed air and the size ($e_1 \times e_2$) of the air exhaust port constant at 2.5 kgf/cm$^2$ and 4.55×1, respectively.

Table 2 also shows the results of experiments (Experiment Nos. 14–15) in which in the USP type having two air supply ports of 1.2 mm in diameter, the pressure of supplied compressed air was changed.

In addition, Table 2 also presents the results of experiments (Experiment Nos. 16–17) in which in the USP type having two air supply ports of 1.2 mm in diameter, the size of the air exhaust ports was changed under the condition for the pressure of supplied compressed air (1 kgf/cm$^2$) in Experiment No. 14.

As is evident from Table 2, the model of the invention type (Experiment Nos. 9–12) was found to exhibit superb advantages over the model of the USP type (Experiment No. 13) under both the first evaluation standard and the second evaluation standard. This indicates that mere enlargement of the cross-sectional area of an air supply port cannot provide a handpiece of excellent characteristics. In Experiment No. 9 directed to the invention type, the importance of an analysis under both the first evaluation standard (X/Y) and the second evaluation standard (X.X/Y) upon evaluation of the performance as described above is understood.

In Experiment Nos. 9–12, the data for $d_1'$ are those obtained when $d_1$ was changed from 150 μm to $d_1'$ (1150–600 μm) in the model of the invention type, in other words, only the value of $d_1$ was brought close to the design concept of the conventional art. A substantial reduction in performance is envisaged.

In Experiment No. 13 directed to the USP type, the supply air volume Y (Y=71.0l/min) gave unduly heavy load to the air supply system. It is Experiment Nos. 14–15 that the pressure of supplied compressed air was changed to improve the unduly heavy load and an investigation was conducted to determine whether preferred results would be obtained by the U.S. type or not. As the results indicate, fairly good results are obtained by adjusting the condition for the pressure of air to be supplied. These improved data of the USP type are better than those obtained by changing $d_1$ to $d_1'$ in the experimental model of the invention type but are still far inferior to the data of the experimental model of the invention type. Further, the improved data of the USP type show the tendency of some improvements over the conventional type in Table 1 (Experiment Nos. 5–8).

It is Experiment Nos. 16–18 that since Experiment No. 14 directed to the USP type showed some improvements over Experiment No. 13 as described above, the conditions in Experiment No. 14 were changed to determined whether better results would be available. As the results indicate, some improvements (Experiment No. 17) are observed but the experimental model of the USP type is far inferior in performance to the experimental model of the invention type.

As is evident from Tables 1 and 2 and also from the above discussions on the experimental results, the invention type can bring about excellent effects compared with the conventional type and the USP type.

For example, as is readily understood from a comparison between the invention type and the conventional type, the invention type can substantially improve the rotational speed (in other words, torque) by a small supply air volume (from 424,000 rpm in Experiment No. 7 to 490,000 rpm in Experiment No. 3), in other words, the invention type can provide the same rotational speed as the conventional type at a supply air pressure or a supply air volume extremely lower or smaller than that set for the conventional type. The invention type can therefore bring about advantageous effects such as:

The noise of rotation can be reduced (a reduction in the noise produced from a handpiece).

The requirement of high pressure resistance for an air supply tube can be lessened.

An air supply tube with higher flexibility can be used, leading to an improvement in handling ease.

Power consumption of a fluid compressing apparatus such as a compressor can be reduced.

Further, the substantial improvement in the maximum rotational speed have made it possible to obtain much greater torque than the conventional handpieces, thereby providing good cutting ability and permitting faster treatment.

In addition, large torque can be obtained even by smaller fluid energy. This has made it possible to fabricate portable handpieces driven by a fluid from a cylinder or handpieces of the rotational speed (in other words, torque) constant-controlled type.

As is indicated by Experiment Nos. 7–8 directed to the conventional type, the conventional type encounters a substantial reduction in performance when reduced in dimensions (a size reduction by narrowing the interval $d_1'$). The invention type, however, permits a dimensional reduction in an air turbine handpiece, so that the present invention can materialize a small but high-performance handpiece with a fluid driven turbine.

As is also evident from the experimental results of the invention type and the USP type, the present invention can provide a high-performance dental air turbine handpiece having the above-described advantageous effects without the difficulty in fabrication or the demerit in economy that two air supply channels (accordingly, two air supply ports) are arranged within the neck portion.

Next, the second embodiment of the present invention will be described.

Figure 14:
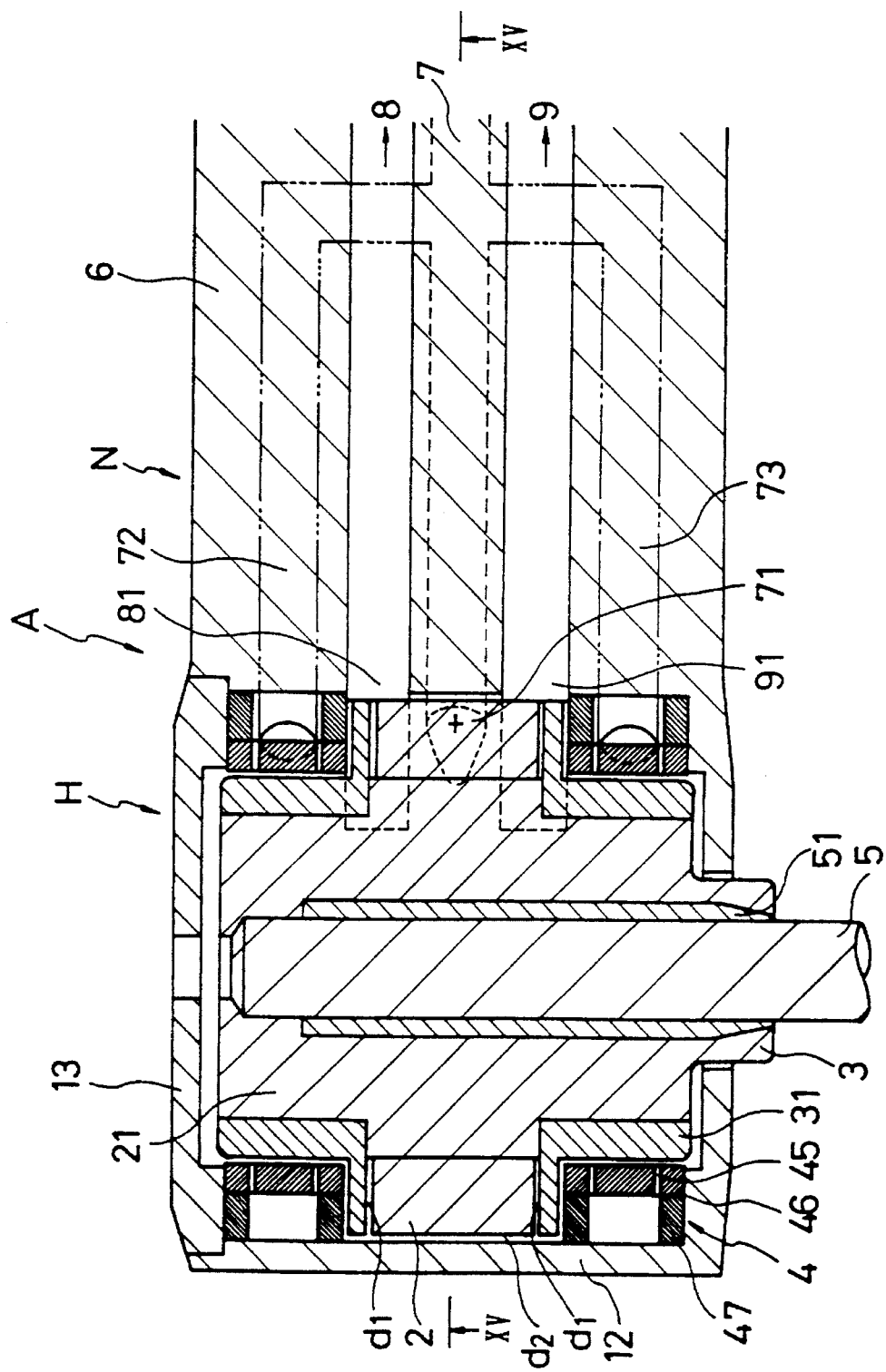
FIG. 14 is a fragmentary vertical cross-sectional view of a small (dental) air turbine handpiece according to a second embodiment of the present invention.
Figure 15:
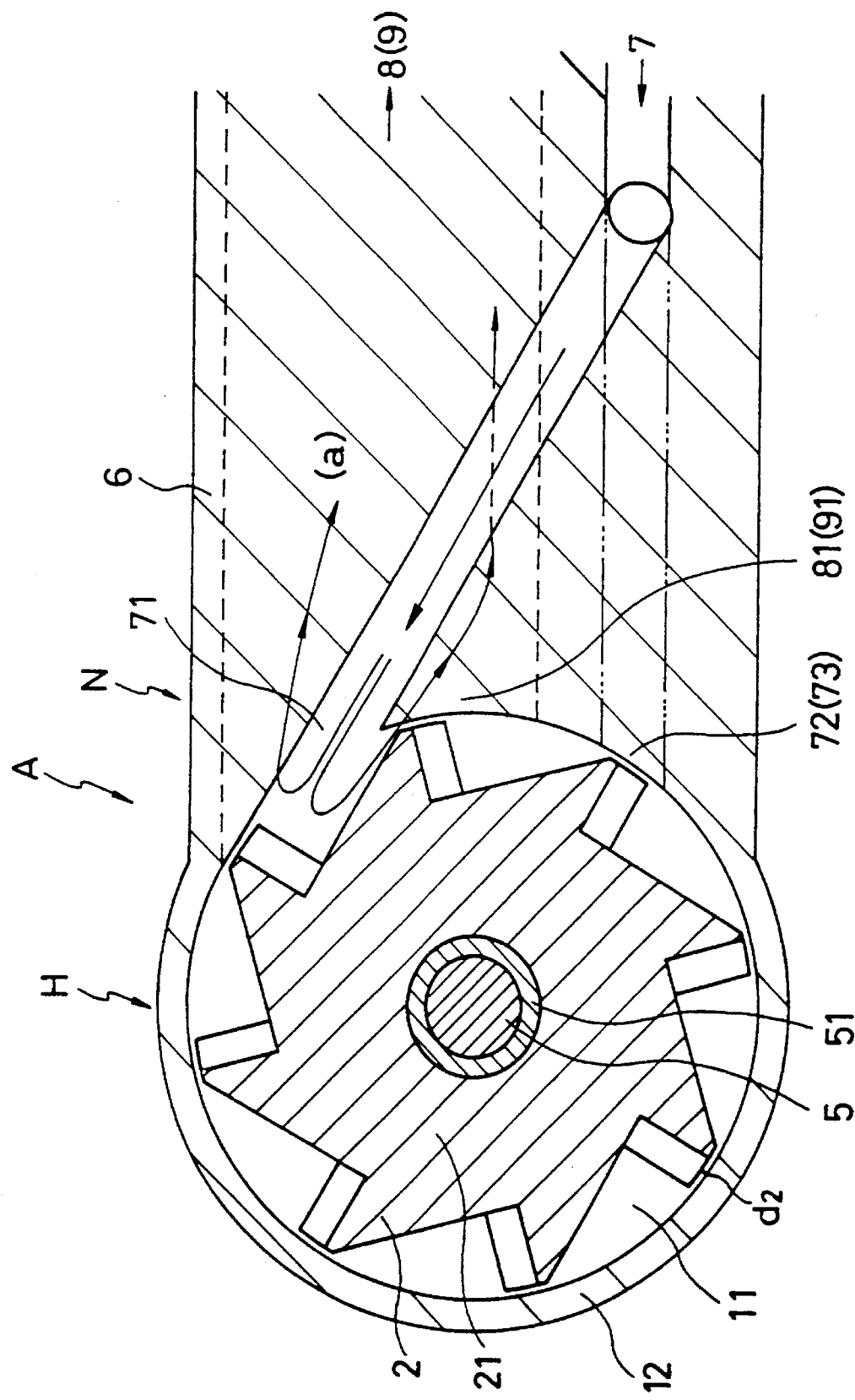
FIG. 15 is a cross-sectional view taken in the direction of arrows XV—XV of FIG. 14.

FIGS. 14–15 illustrates the dental air turbine handpiece A according to the second embodiment of the present invention.

The dental air handpiece A according to the second embodiment is substantially different from the above-described air handpiece according to the first embodiment in the construction of the bearings 4. The remaining construction are substantially the same in both the embodiments.

Described specifically, they are different in that the bearings 4 in the above-described first embodiment use ball bearing units making use of ball bearings while the bearings 4 in the second embodiment employs air bearing units making use of an air stream (air layer).

The bearings 4 which employ the above-described air bearing units are each composed of a bearing 46 defining therethrough radial through-holes 45 and a shaft portion 31 disposed inside the bearing 46 or extending from an inside of the bearing to a side portion of the bearing. This shaft portion may be integral with the turbine rotor shaft 3.

Each bearing 46 is resiliently held on a side wall 12 of a head portion H by a bearing support 47 located on an outer peripheral wall of the bearing.

In the second embodiment, branch channels 72,73 extend from the air supply channel 7 as illustrated in FIG. 14, so that air can be supplied to the air bearing units (i.e., the bearings 46 described above).

By supplying air into gaps between the bearings 46 and the shaft portion 31 through the branch channels 72,73 and the through-holes 45, the shaft portion 31, i.e, the turbine rotor 3 is held in a floated state via layers of air, which was supplied into the gaps, without contacting the bearings 46 so that the turbine rotor is rotatably supported.

In connection with FIG. 14 of the second embodiment, the interval ($d_1$) between the turbine blades and each of the upper and lower, inner walls of the chamber 11 in the first embodiment should be interpreted equivalent to the interval ($d_1$) between the turbine blades 2 and each of upper and lower surfaces of the shaft portions 31. Use of the approach taught by the present invention can make the dental handpiece A of this second embodiment exhibit similar advantageous effects as the above-described handpiece of the first embodiment.

What is claimed is:

1. In a small handpiece with a fluid driven turbine, said handpiece being composed of a head portion and a neck portion connected continuously to said head portion, said head portion having a head defining a chamber therein, turbine blades mounted on a turbine rotor shaft and arranged within said chamber and said turbine rotor shaft rotatably supported in said head via bearing portions, and said neck portion having a main body, a supply channel arranged in said main body to supply compressed fluid to said turbine blades within said chamber and an exhaust channel arranged in said main body to discharge the compressed fluid from said chamber, the improvement comprising:

(i) said supply channel has a single supply port; and (ii) a positional relationship between said single supply port and an exhaust port of said exhaust channel is set so that said exhaust port is arranged at a position proximal to said supply port such that circumferential flow of said compressed fluid after impingement on said turbine blades is prevented.

2. A small handpiece according to claim 1, wherein the overall size of said turbine blades arranged within said chamber of said head is substantially the same as the spatial volume of said chamber.

3. A small handpiece according to claim 1, wherein the overall dimensions of said turbine blades are set so that $d_1$ is not greater than $\frac{1}{10}$ of h where $d_1$ means the interval between said turbine blades and each upper and lower inner walls of said chamber and h means the height of said turbine blades, both as viewed in the direction of an axis of said turbine rotor shaft.

4. A small handpiece according to claim 3, wherein the interval $d_1$ is not greater than 500 μm but greater than 0 μm.

5. A small handpiece according to claim 4, wherein the interval $d_1$ is from 100 μm to 200 μm.

6. A small handpiece according to claim 1, wherein the overall dimensions of said turbine blades are set so that $d_1$ is not greater than 2.5 times $d_2$ but greater than 0 times $d_2$ where $d_1$ means the interval between said turbine blades and each of upper and lower inner walls of said chamber as viewed in the direction of an axis of said turbine rotor shaft and $d_2$ means the interval between the turbine blades and a peripheral inner side wall of said chamber as viewed in a direction perpendicular to said axis of said turbine rotor shaft.

7. A small handpiece according to claim 1, wherein said interval $d_2$ is 150 μm.

8. A small handpiece according to claim 1, wherein said single supply port of said supply channel has a size not greater than 50% but greater than 0% of the height h of said turbine blades as viewed in the direction of an axis of said turbine rotor shaft.

9. A small handpiece according to claim 1, wherein the positional relationship between said single supply port of said supply channel and said exhaust port of said exhaust channel is set so that said exhaust port is arranged at a position vertically proximal to said supply port.

10. A small handpiece according to claim 1, wherein the positional relationship between said single supply port of said supply channel and said exhaust port of said exhaust channel is set so that said exhaust port is arranged immediately above said supply port.

11. A small handpiece according to claim 1, wherein the area of opening of said exhaust port is greater than that of said single supply port.

12. A small handpiece according to claim 1, wherein said single supply port of said supply channel is arranged at a position so that the compressed fluid from said supply port is injected against substantially central parts of said turbine blades as viewed in the direction of an axis of said turbine rotor shaft.

13. A small handpiece according to claim 1, wherein said bearing portions are ball bearings.

14. A small handpiece according to claim 1, wherein said bearing portions are air bearings.

15. A small handpiece according to claim 1, wherein said head and said main body of said neck portion are made of a synthetic resin.

16. A small handpiece according to claim 1, further comprising a tool for medical or dental treatment, said tool being detachably mounted on said turbine rotor shaft.

17. A small handpiece according to claim 1, wherein the positional relationship between said single supply port of said supply channel and said exhaust port of said exhaust channel is set so that said exhaust port is arranged at a position horizontally proximal to said supply port.

18. A small handpiece according to claim 1, wherein the positional relationship between said single port of said supply channel and said exhaust port of said exhaust channel is set so that said exhaust port is arranged immediately below said supply port.

* * * * *